United States Patent [19]

Smith

[11] Patent Number: 5,241,859
[45] Date of Patent: Sep. 7, 1993

[54] FINDING AND EVALUATING ROCK SPECIMENS HAVING CLASSES OF FLUID INCLUSIONS FOR OIL AND GAS EXPLORATION

[75] Inventor: Michael P. Smith, Tulsa, Okla.

[73] Assignee: Amoco Corporation, Chicago, Ill.

[21] Appl. No.: 546,346

[22] Filed: Jun. 29, 1990

[51] Int. Cl.$^5$ ............................................. G01N 33/24
[52] U.S. Cl. ..................................... 73/153; 73/53.01; 356/128; 250/301
[58] Field of Search .................... 73/153, 23.37, 23.38, 73/19.01, 53.01, 151; 356/128; 250/301

[56] References Cited

U.S. PATENT DOCUMENTS

| | | | |
|---|---|---|---|
| 2,531,083 | 11/1950 | Smith | 73/19.01 |
| 3,418,841 | 12/1968 | Issenmann | 73/19.01 |
| 4,609,821 | 9/1986 | Summers | 250/253 |
| 4,790,180 | 12/1988 | Sinnokrot | 73/153 |
| 4,814,614 | 3/1989 | Tsui | 250/301 |
| 4,856,351 | 8/1989 | Smith et al. | 73/863.21 |
| 4,860,836 | 8/1989 | Gunther | 73/153 |
| 4,898,831 | 2/1990 | Smith et al. | 436/32 |
| 4,916,314 | 4/1991 | Smith et al. | 250/307 |
| 5,012,674 | 5/1991 | Millheim et al. | 73/153 |
| 5,049,738 | 9/1991 | Gergely et al. | 250/301 |

FOREIGN PATENT DOCUMENTS 0414564  8/1990  European Pat. Off. ................ 33/24

OTHER PUBLICATIONS

Shepherd et al. "A Practical Guide to Fluid Inclusion Studies", 1985, pp. 219-222.
Barker, et al, "Mass Spectrometric Determination of Gases in Individual Fluid Inclusions in Natural Minerals", Reprint from Analytical Chemistry, 1986, 58, pp. 1330-1333.
Bloss, et al, "An Introduction to the Method of Optical Crystallography", (1961), pp. 50-52.
Burruss, R. C., "Hydrocarbon Fluid Inclusions in Studies of Sedimentary Diagenesis", from Hollister et al. (eds) *Short Course in Fluid Inclusions: Applications to Petrology*, vol. 6, Mineralogical Assoc. of Canada, pp. 138-156 (1981).
Haszeldine et al, (1984) "Dating Diagenesis in a Petroleum Basin, A New Fluid Inclusion Method", Nature, vol. 307, pp. 354-357.
Kvenvolden, K. A., "Fluid Inclusions in Quartz Crystals from South-West Africa", Geochimica et Cosmochimica Acta, 1971, vol. 35, pp. 1209-1229.
Schaeffer, H. F., "Microscopy for Chemists", (1953) pp. 85-87.

*Primary Examiner*—Hezron E. Williams
*Assistant Examiner*—Michael Brock
*Attorney, Agent, or Firm*—Richard A. Kretchmer; Frank J. Sroka

[57] ABSTRACT

A rock specimen is selected from many rock specimens based on composition of released fluid inclusion volatiles being indicative of a selected class of fluid inclusions therein. Compositions of selected classes of inclusions or of selected individual fluid inclusions in the selected rock specimen are further characterized and the resulting information used in exploring for oil and gas.

8 Claims, 21 Drawing Sheets

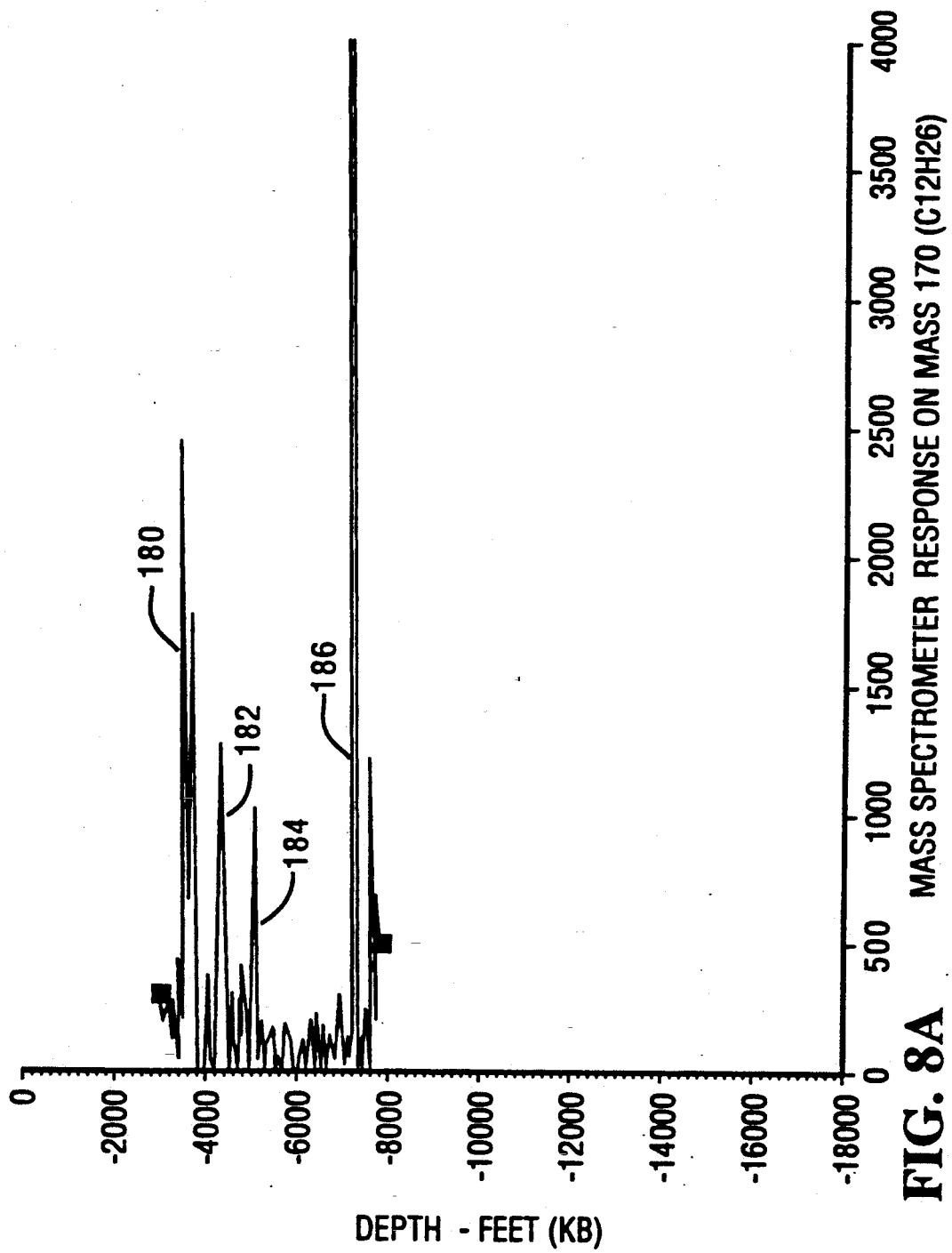

FINDING AND EVALUATING ROCK SPECIMENS HAVING CLASSES OF FLUID INCLUSIONS FOR OIL AND GAS EXPLORATION

FIELD OF THE INVENTION

The invention relates to exploring the earth's subsurface for producible hydrocarbons. In a particular aspect, the invention relates to determining quality of oils in microscopic fluid inclusions in reservoir or other rock.

SETTING OF THE INVENTION

Producible accumulations occur when hydrocarbons generated from source rock migrate through the subsurface to a trap where they are accumulated. During migration, small quantities of the migrating hydrocarbons are trapped in microscale fluid inclusions in the rock matrix. These inclusions preserve a record of migration which could provide valuable information to the explorationist indicating whether oil has migrated through an area and through which strata, whether potential hydrocarbon accumulations are of commercial interest, and whether the hydrocarbons are the same as or different from hydrocarbons known to occur in the region.

Analysis of this record would require finding particular strata containing hydrocarbon particularly oil fluid inclusions, evaluating the quality of the inclusion hydrocarbons, and comparing the quality to oil known to occur in the region.

Oil fluid inclusions can be identified from thin polished mineral sections using a microscope. However, using a microscope to find formations characterized by occurrence of oil fluid inclusions would require that mineral thin sections be made at many different depths and examined for occurrence of oil inclusions. A method is needed for scanning rock samples from multiple different depths in the earth and rapidly identifying strata and formations characterized by abundant oil fluid inclusions without first preparing thin sections for microscopic evaluation. In a more general aspect, a method is needed for rapidly identifying specimens characterized by relative abundance of compositions indicative of a selected class of fluid inclusions so that the compositions of the selected class or of individual inclusions in the class can be further characterized and investigated for information useful to the explorationist.

Fluid inclusions in sedimentary rock are generally small, almost always less than 10 microns, and mostly less than 5 microns in diameter. Extracting oil from individual fluid inclusions for analysis is work-intensive. On the other hand, if the extract is from multiple fluid inclusions which may have formed at several different times and may contain several different oils of different quality, interpretation is difficult. Therefore, for evaluating quality of fluid inclusion oils, analysis of individual fluid inclusions is preferred.

Fluorescence microspectrophotometry (FM) is sometimes used for evaluating quality of oil contained in individual fluid inclusions since this technique does not require extraction of hydrocarbons but can be determined from mineral thin sections. However, FM results are influenced by factors other than quality of oil. Thus, for example, FM results are significantly affected by trace amounts of elements or compounds which cause fluorescence. Thus, for example, aromatic compounds causing fluorescence can be present in gases, oils, and in degraded oils apparently indicating a similar API gravity according to the FM technique. In fact, the API gravities of the three are quite different.

A method for more directly evaluating oil quality in individual fluid inclusions without extraction is needed.

SUMMARY OF THE INVENTION

According to one aspect, the invention relates to instrumentally scanning rock samples from multiple different locations in the earth and selecting from the rock samples one or more rock specimens based on abundance of occurrence of a selected class of fluid inclusions therein.

According to this aspect, fluid inclusion volatiles are released from samples of each of a plurality of rock samples from different locations in the earth, the composition of the released volatiles is determined, one or more rock specimens is selected from rock samples characterized by relative abundance of compositions representative of occurrence of a selected class of fluid inclusions, and composition of fluid inclusions in the thus selected rock specimens are further analyzed for information pertinent to oil and gas exploration and development.

According to another aspect, the invention relates to a method for determining quality of oils contained in selected individual fluid inclusions in a rock specimen which can provide reliable quality estimates from single hydrocarbon fluid inclusions even down to as small as 1 micron in diameter or smaller.

According to this aspect, a rock specimen containing oil fluid inclusions is evaluated to determine the quality of oil in selected individual fluid inclusions. For each selected individual fluid inclusion, the temperature is determined for which the refractive index of oil in the fluid inclusion is about equal to the refractive index of the adjacent mineral of the rock specimen. $T_{o^n m = 1}$ is used herein to refer to the temperature at which the refractive index of oils "o" in the inclusion relative to the refractive index "n" of adjacent mineral "m" (i.e., the ratio of absolute refractive indexes) is about unity, i.e., $o^n m = 1$. The quality of a reference oil having the same or about the same $T_{onm=1}$ for the same mineral or a mineral having about the same index of refraction is used as a measure of the quality of the oils in the selected fluid inclusion.

The resulting quality information can be used to evaluate whether accumulations of the oil would be of commercial interest, whether the oil in the inclusion is the same as or different from oil known to occur in the region; and generally utilized in determining further exploration or production activities.

BRIEF DESCRIPTION OF THE DRAWINGS

FIG. 8A illustrates for a first well a plot of depth versus an MCR indicator of oil in collective fluid inclusion volatiles of a plurality of rock samples.

DESCRIPTION OF THE INVENTION

Figure 1:
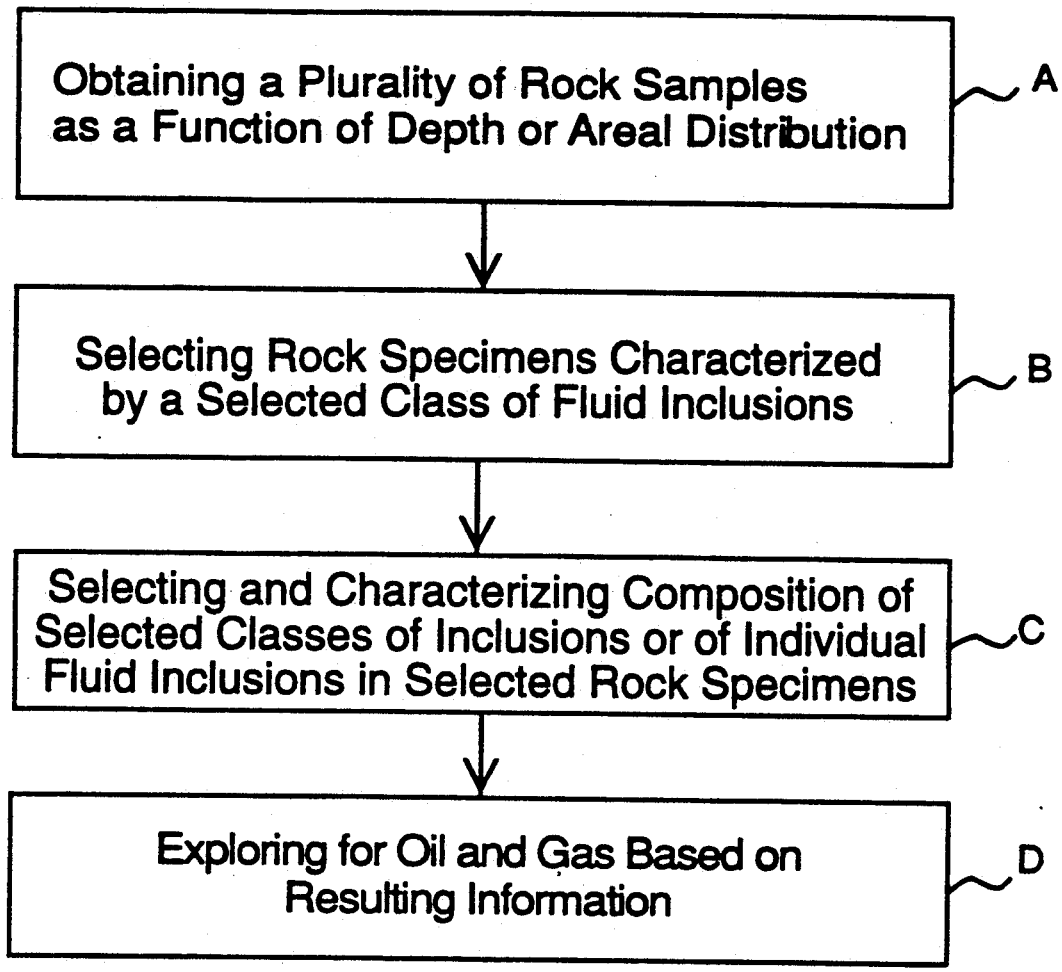
FIG. 1 illustrates generally a first aspect of the invention.

Referring now to FIG. 1, FIG. 1 illustrates generally a first aspect of the invention including obtaining rock samples as a function of depth or areal distribution A, selecting rock specimens characterized by a selected class of fluid inclusions B, selecting and characterizing composition of specific classes of fluid inclusions or selected individual fluid inclusions in selected minerals specimens C, and D utilizing the resulting information in exploring for oil and gas.

Figure 1A:
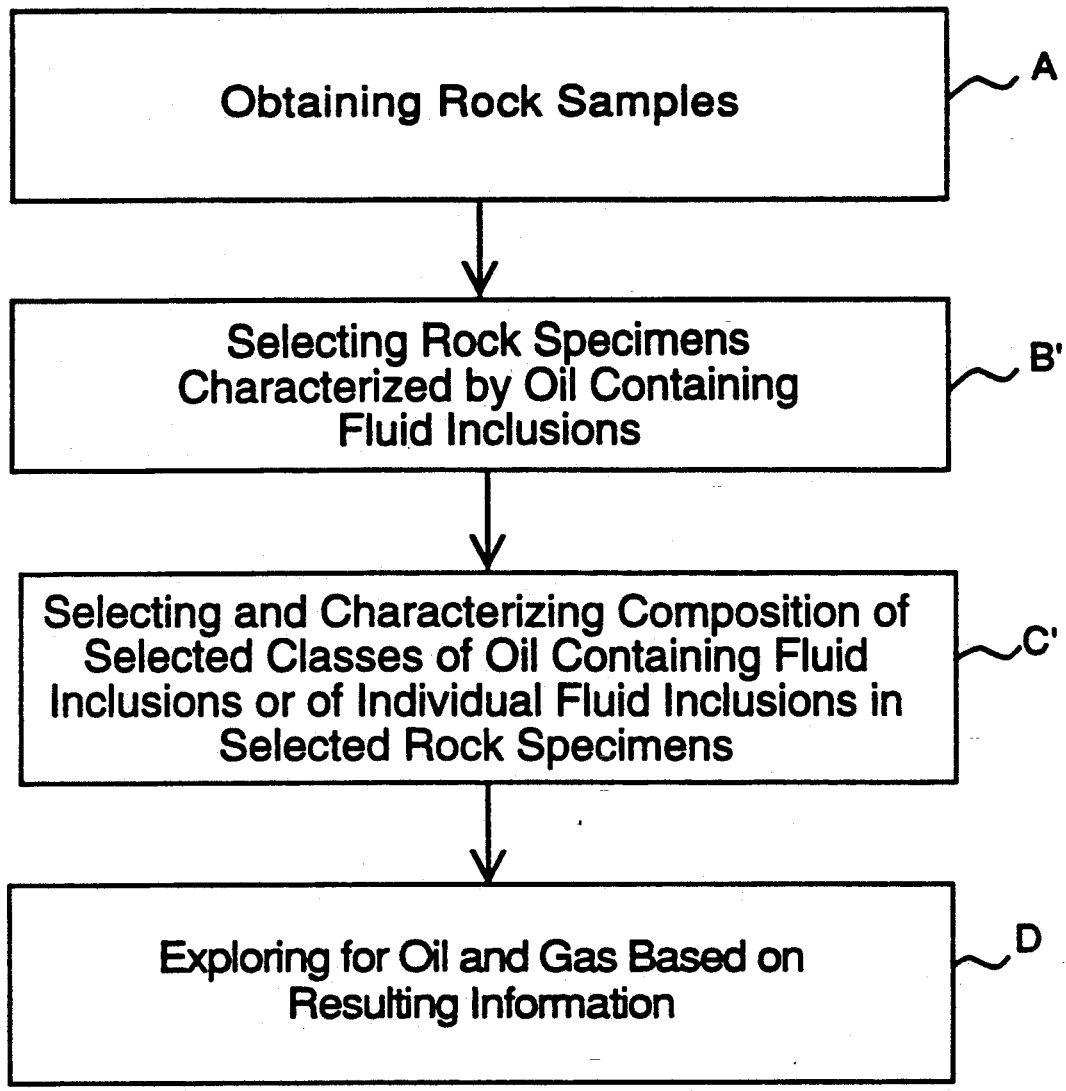
FIG. 1A illustrates generally a preferred embodiment of FIG. 1.

As illustrated in FIG. 1A, according to a specific aspect of the invention, steps B and C can comprise selecting rock specimens characterized by relative abundance of hydrocarbon or oil fluid inclusions and then further characterizing the composition of selected classes of oil inclusions or of individual fluid inclusions.

A. Obtaining Rock Samples

Figure 2:
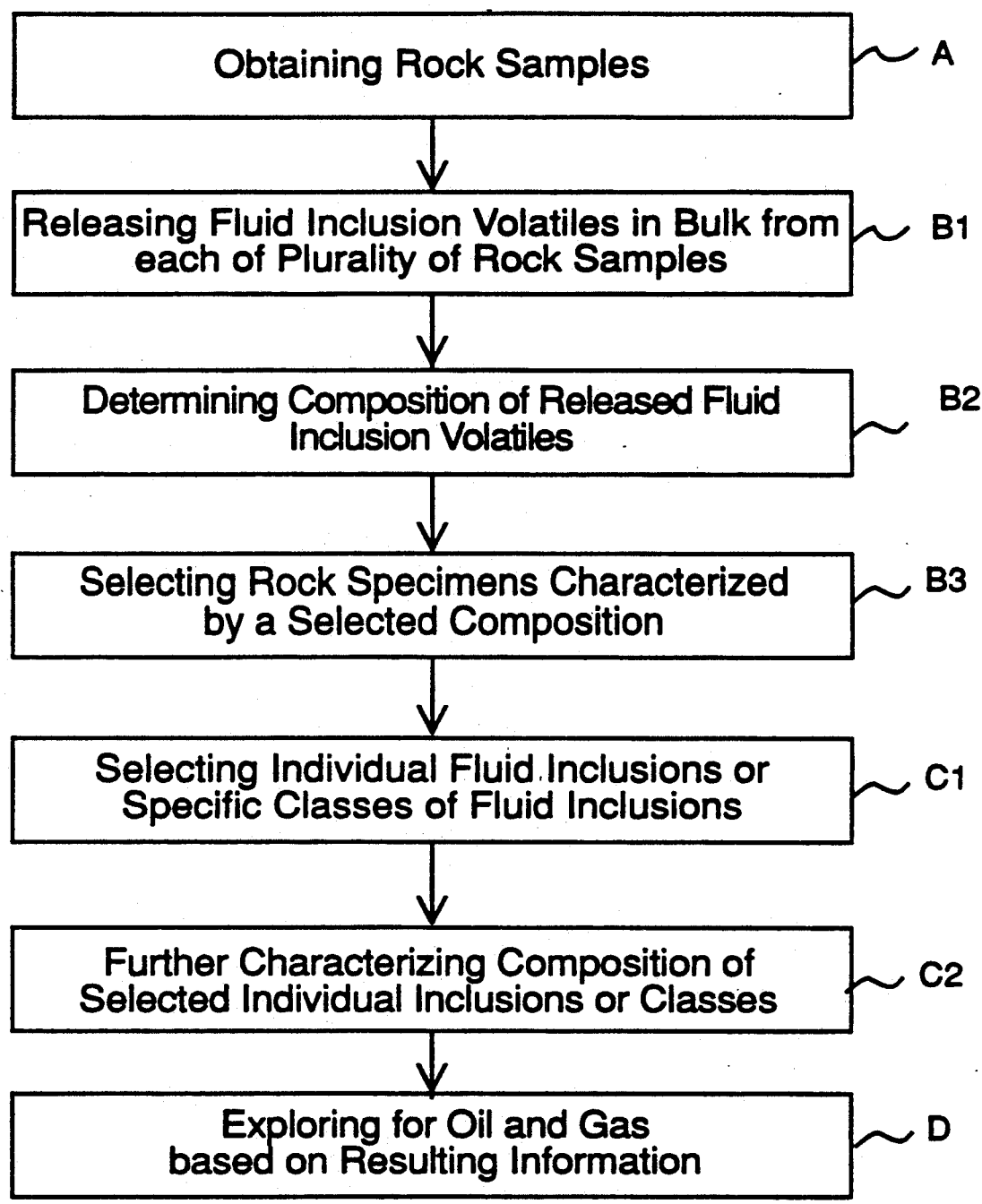
FIG. 2 represents FIG. 1 with steps B and C illustrated in greater detail.

As illustrated in FIGS. 1 and 2, a step A of the invention relates to obtaining a plurality of rock samples as a function of depth or areal distribution in the earth.

The rock samples can be washed drill cuttings, cores, outcrop samples, soil samples, sidewall cores, and the like. Preferably, drill cuttings are used. Drill cuttings are widely available and allow investigation of substantially the entire length of a borehole.

Where more than one well is present in an area of exploration interest, areal samples are frequently also available.

Figure 1B:
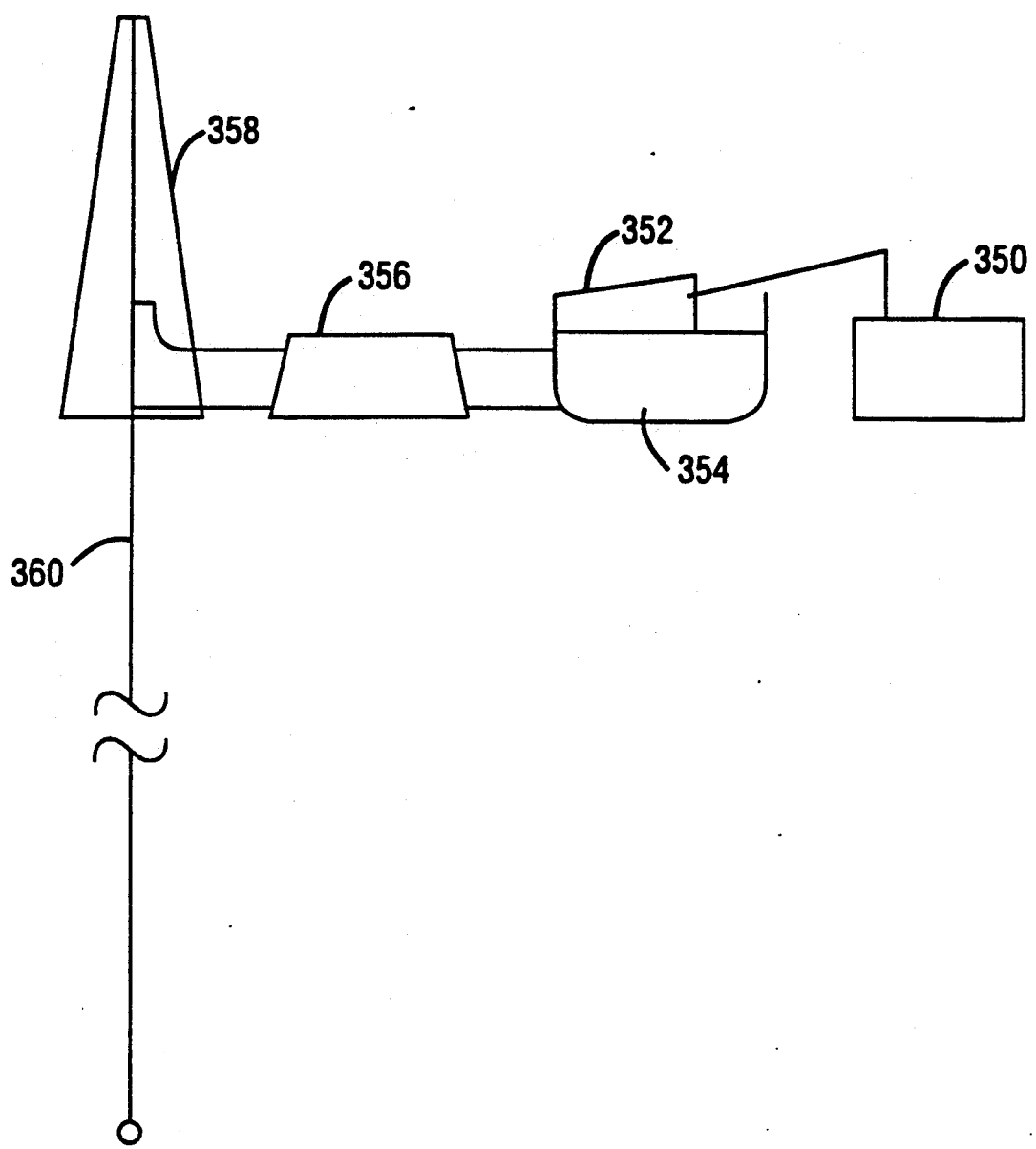
FIG. 1B illustrates collection of drill cuttings.

Referring now to FIG. 1B, FIG. 1B illustrates that cuttings can be collected at intervals during drilling of well 360 by rig 358. Mud pump 356 can return drilling mud carrying drill cuttings to shale shaker 352 and mud pit 354. Drill cuttings can be periodically collected by cuttings collector 350. Drill cuttings have been archived from many existing wells so that new wells or samples are often not needed.

The drill cuttings can be from wells drilled with oil-based or water-based muds since, as discussed below in reference to FIGS. 6A and 6B, methods for releasing in bulk and determining composition of fluid inclusion volatiles can distinguish background volatiles from fluid inclusion volatiles. Solvents or heating, for example, overnight at 200° C., may also be used to extract drilling mud residues prior to releasing and analyzing fluid inclusion volatiles.

About 10 cubic centimeters or less of each rock sample are suitable for analyses using the invention. Rock samples representative of at least every 200 ft, 100 ft, 50 ft, 20 ft, 10 ft or less provide an adequate frequency of sampling for good results. Sixty-foot spacing has provided excellent results in many runs. More frequent sampling can also be advantageous. For regional investigations, each of multiple spaced apart wells can be sampled along substantially the entire depth or along a zone of particular interest, for example, a particular formation. Preferably, 50 to 100 or more specimens spanning a depth or areal domain of interest are selected; fewer can also be used.

B. Selecting Rock Specimens Characterized by a Selected Class of Fluid Inclusions As illustrated at step B of FIGS. 1 and 1A, the invention in one aspect relates to selecting one or more rock specimens characterized by a selected class of fluid inclusions from the plurality of rock samples. As shown in FIG. 1A, the selection can be based on occurrence of oil-containing fluid inclusions therein.

Fluid inclusions are trapped fluids occluded in the matrix of rocks in tiny cavities which do not contribute to the rock's pore system. Fluid inclusions are classified as hydrocarbon or oil inclusions when liquid hydrocarbons are predominant, aqueous inclusions when liquid water is predominant, and gaseous when gases are predominant. Mixed inclusions also occur.

Fluid inclusions are portions of ambient liquid and gases trapped in minerals during mineral growth or fracture healing and can be used to characterize the environment in which the fluid inclusions were formed. Sedimentary reservoir rock is characterized by large numbers of fluid inclusions usually smaller than 10 microns diameter and of different generations, i.e., formed at different times and representing different environments. The frequency of occurrence of inclusions per unit volume of sedimentary rock sample varies considerably, but can be reasonably estimated to be on the order of $10^3$ to $10^9$ inclusions per cubic centimeter of rock. This order of magnitude of occurrence of fluid inclusions in sedimentary rocks such as carbonates, sandstones, and shales is referred to herein as myriad fluid inclusions and volatiles released indiscriminately from myriad fluid inclusions are referred to as released in bulk or as bulk or collective fluid inclusion volatiles.

Figure 1C:
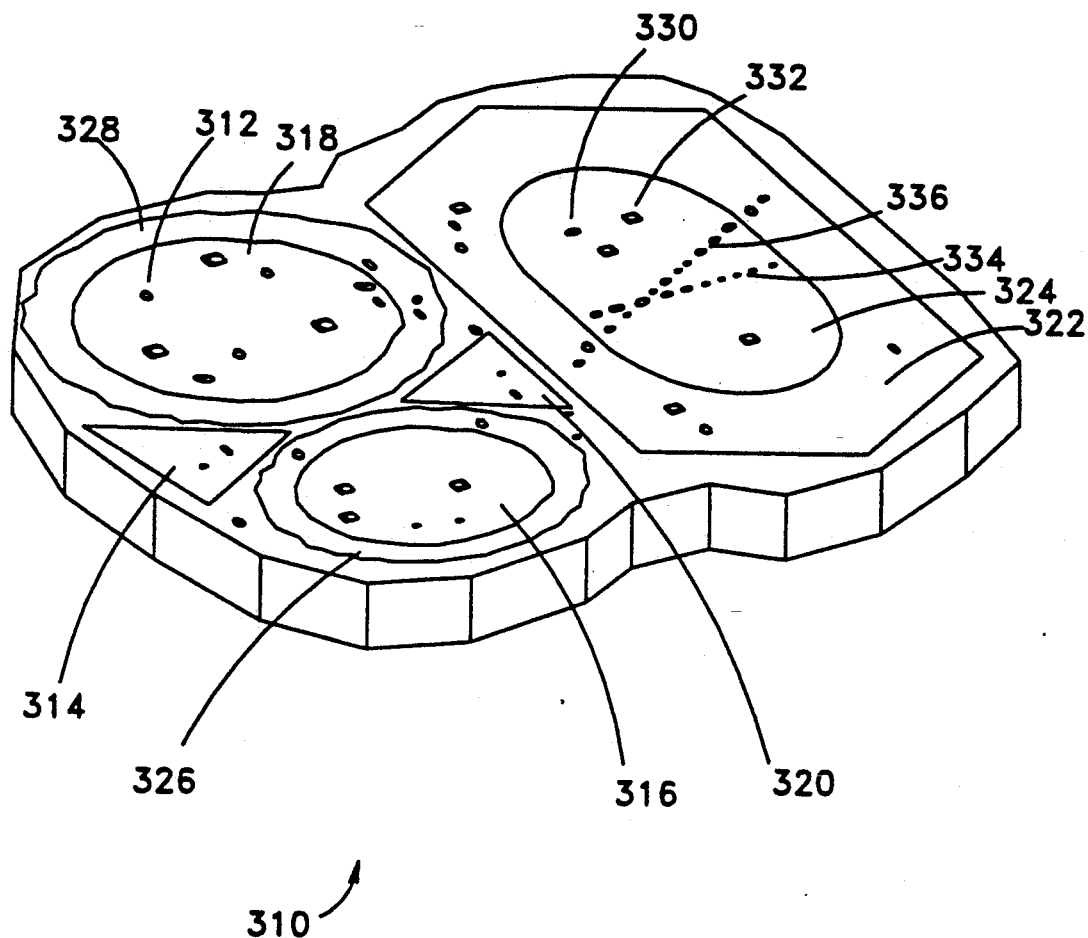
FIG. 1C illustrates minerals and fluid inclusions as seen in a thin mineral section.

Referring now to FIG. 1C, FIG. 1C illustrates fluid inclusions such as might be observed in a mineral thin section specimen 310 taken from a sedimentary rock sample. Section 310 is a cut section approximately 0.03-1.0 millimeter thick polished on both sides and mounted on a glass slide (not shown). Section 310 is illustrated magnified as if seen through a microscope. The fluid inclusions, like inclusion 312, formed in the various mineral growths in sample 310 are under 10 microns in diameter. Sample 310 includes a plurality of mineral growths, like minerals 314, 316, 318, 320, 322, and 324. Minerals 316 and 318 each include a mineral overgrowth 326 and 328, which acts and is referred to as a cement.

Mineral 324 includes a plurality of primary inclusions like inclusions 330 and 332 formed during the initial growth of mineral 324. A healed crack 334 is formed in mineral 324, and a healed crack 336 is formed in mineral 322 and in mineral 324. Crack 334 was formed in mineral 324 after the original growth of mineral 324, and thus after the primary inclusions, like inclusions 330 and 332 were formed. Crack 336 was also formed in minerals 322 and 324 after the formation of the primary inclusions in both minerals 322 and 324. Each of cracks 334 and 336 have a plurality of secondary inclusions, as shown, formed along the cracks. These secondary inclusions were formed during healing of cracks 334 and 336 when mineral growth developed in the cracks. Thus, the secondary inclusions in crack 334 trap environmental fluids at a later time than the primary inclusions in mineral 324 and the secondary inclusions along crack 336 trap fluids at a later time than when the environmental fluids were trapped in the primary inclusions in both minerals 322 and 324. Moreover, the secondary inclusions in crack 334 may well be formed at a time far removed from those formed in crack 336, and thus, the secondary inclusions in crack 334 may be of a different generation than those along crack 336. Likewise, the primary inclusions formed in the various minerals and cements in sample 310 may be formed at vastly different times from one another, thus trapping the environmental fluids present at the time of formation.

Referring now to FIG. 2, FIG. 2 illustrates that step B of FIGS. 1 and 1A can include steps B1 releasing fluid inclusion volatiles in bulk from each of a plurality of rock samples, B2 determining composition of released fluid inclusion volatiles for each rock sample, and B3 selecting rock specimens characterized by a selected composition.

B1—Releasing Fluid Inclusion Volatiles in Bulk from Rock Samples

As indicated, an aspect of the invention can include a step of releasing fluid inclusion volatiles in bulk from each of a plurality of rock samples. The release of fluid inclusion volatiles in bulk can be accomplished by any suitable technique including those known to those skilled in the art such as placing a rock sample in a metal tube, crimping the ends, impacting to release volatiles, and opening the tube and collecting the volatiles for analysis. Preferably, the release of bulk volatiles is achieved as hereinafter described.

Figure 3A:
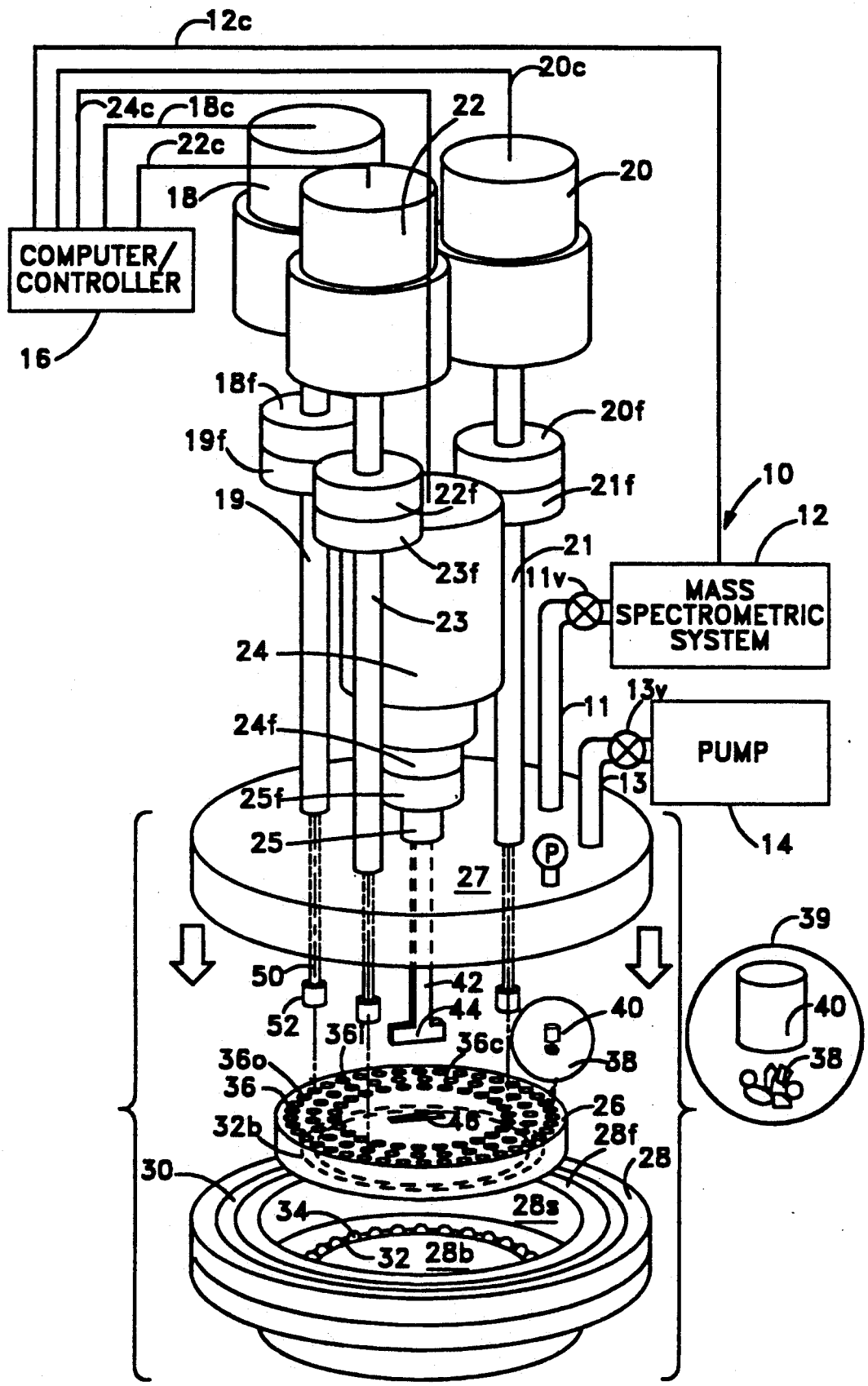
FIG. 3A illustrates, in exploded view, a preferred autosampler system for automated release and composition analysis of collective fluid inclusion volatiles samples from each of a plurality of rock samples.

Referring now to FIG. 3A, FIG. 3A illustrates in exploded view an autosampler 10 configured with controller 16 and spectrometer 12 for releasing, delivering and analyzing composition of a plurality of fluid inclusion volatiles samples. Volatiles samples released in bulk from myriad fluid inclusions in a sedimentary rock sample may also be referred to as collective volatiles or collective fluid inclusion volatiles.

System 10 includes upper housing 27 and lower housing 28 having seal 30 therebetween for forming evacuable chamber 60 (see FIG. 3B) when housings 27 and 28 are aligned and joined. It is desirable for chamber 60 to be as small as feasible. Seal 30 can be an oxygen-free high conductivity copper gasket. Housings 27 and 28 can be adapted with knife edges for sealing by engaging gasket 30. Evacuable chamber 60 has an outlet 11 with valve 11v which delivers released volatiles to spectrometer 12 as they are being released.

Vacuum pump 14 places vacuum stage 10 under a vacuum at the start of a sequence of analyses. Thereafter, the system can be maintained under vacuum by pumps 15' associated with the mass spectroscopic system. See FIG. 4A.

Lower housing 28 comprises flange 28f, sidewall 28s, and base 28b. Base 28b has a groove 32 therein holding bearings 34. Circular carousel 26 is adapted with a plurality of sample chambers 36 therein and centered slot 46 for engagably receiving shaft key 44 on stepper motor shaft 42. Asymmetric tab 44 fits into notch 46 in the carousel. Asymmetry of tab 44 and notch 46 assure that the carousel 26 is positioned in the autosampler so that each sample has a uniquely determined position. Carousel 26 has groove 32b for engaging bearings 34 in groove 32a in base 28b. When carousel 26 is placed in lower housing 28, grooves 32b and 32a cooperate to align the carousel 26, and bearings 34 provide for rotation of carousel 26 in response to motor 24 turning shaft 42 having key 44 engagably connected with slot 46.

Sample chambers 36 are each effective for receiving a rock sample 38 and for maintaining it during volatiles release in a confined space between the walls and base of the chamber and the impacting means.

A typical rock sample is less than 10 cc (cubic centimeters) in volume which provides sufficient material for several runs, if necessary. Core and outcrop samples are usually broken prior to analysis while drill cutting samples can be used directly. Individual samples for analysis generally range from about 1/100 to about ¼ cc, typically about 1/25 to about ⅛ cc. Use of approximately equal samples by volume or by weight is preferred for each analysis since such enhances displays (reduces data scatter) of abundance of selected volatiles plotted as a function of the depths of the respective rock samples.

Depths or areal locations are recorded by entry into a computer such as controller 16 as the samples are loaded into predetermined sample chambers in the carousels. The depths can later be transferred to another computer such as a mainframe for analysis of resulting data if desired.

Three pneumatic rams 18, 20, and 22 are illustrated passing through upper housing 27. More or fewer rams can be used. Illustrated carousel 26 has three concentric rings of sample chambers 36, and each pneumatic ram aligns with a respective concentric ring of sample chambers. Ram 19 is illustrated with plunger 52 and ram tip 54. Ram 19 aligns with outer ring 36o; ram 20 aligns with intermediate ring 36i, and ram 22 aligns with central ring 36c. When a sample chamber 36 is aligned with a respective ram, the ram is actuated to impact a sample 38 in the chamber effective for releasing a collective volatiles sample. Preferably, each sample chamber is also provided with a sample chamber slug 40 to prevent cross contamination of samples during impacting. Slug 40 can be considered part of the impacting means. Sample 38 and slug 40 are shown enlarged in circle 39 for clarity. However, slug 40 is adapted to cover sample 38 in chamber 36 while permitting volatiles to escape through an annulus between slug 40 and the wall of chamber 36. While only one slug 40 and sample 38 are shown, there will usually be as many slugs 40 and samples 38 as chambers 36.

Figure 3B:
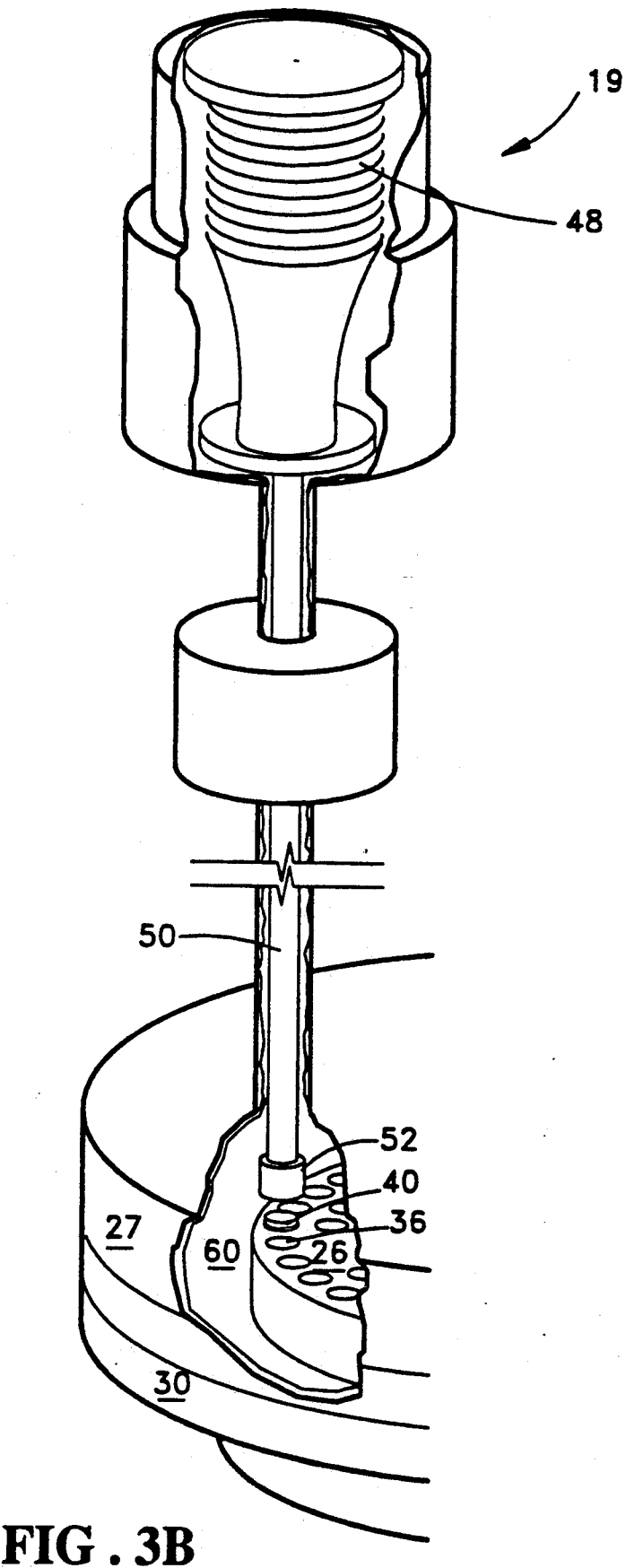
FIG. 3B illustrates a cutaway view of a portion of the autosampler 10 of FIG. 3A as assembled.

Referring now to FIG. 3B, FIG. 3B illustrates in greater detail the operation of the rams. Pneumatic ram 19 as indicated is aligned with the outer row 36o of sample chambers on carousel 26. In response to a signal via line 18c from controller 16 (see FIG. 3A), the pneumatic ram bellows 48 expand, driving shaft 50 and plunger 52 into contact with the slug 40, impacting sample 38 in chamber 36. Impacting of the sample may occur one or more times, preferably multiple times under control of controller 16 to ensure release of substantially all fluid inclusion volatiles. The released fluid inclusion gases then are transported within chamber 60 through a space between the lower surface of upper housing 27 and the upper surface of the carousel 26 to mass spectrometer 12 for analysis. Mass spectrometer 12 can be controlled by computer controller 16 as illustrated by line 12C.

Impacting of the sample preferably occurs while the sample is closely confined by a slug 40 in a chamber 36. The impact can be any impact sufficient for releasing a collective fluid inclusions volatile sample, for example, by crushing, pulverization, and the like. Preferably, the impact is effective for causing a deformation or concussion of the sample effective for releasing a collective volatiles sample substantially without crumbling or powdering the sample. For most drill cuttings run, an impact of about 400 pounds per square inch is effective. The result of crushing is preferably a rock sample deformed and shaped by the sample chamber and the crushing means into a compacted aggregated mass.

Impacting can take place virtually instantaneously up to about 10 seconds or even longer. Ten or twelve seconds have provided highly satisfactory results. In such case, the plunger impacts the rock sample and maintains fluid inclusion deforming pressure thereon for 10 or 12 seconds, for example. When iterative impacting is employed, all of the iterations can be made to occur in 10 seconds or 12 seconds or less if desired. Alternatively, the sample can be impacted and pressure maintained for a period of time such as 10 or 12 seconds, released for a period of time such as 10 or 12 seconds, and again impacted and pressure maintained and released one or more additional times. Impacting generally can be for a time effective for releasing a volume of fluid inclusion gases. Release of substantially all, or at least a preponderance of, fluid inclusion volatiles is preferred.

As illustrated, the invention includes a controller 16 for controlling sampler 10, for example, by controlling motor 24, rams 18, 20, 22, to release sequentially in bulk from each of a plurality of rock samples fluid inclusion components and for controlling mass spectrometer 12 for removing and analyzing the released fluids.

In pumpdown configuration value 13v is open and value 11v is closed; in automated sampling configuration, 11v is closed and 13v is open. Autosampler 10 can be heated to maintain the samples at about 150° C. during operation. Inlet and outlet lines to mass spectrometer system 12 can also be heated to about 150° C. Alternatively, room or ambient temperature operation can be used to facilitate equilibration of the system. When room temperature operation is used, a polymer vacuum seal can be used instead of a metal gasket for seal 30 in FIG. 3A.

The analysis temperature can be any temperature effective for volatilizing particular molecules of interest up to a temperature less than that at which thermal decapitations causes release of fluid inclusion volatiles. For oil and gas exploration, temperatures in the range of about 150° to about 200° C. are particularly advantageous for volatilizing of hydrocarbons.

For operation autosampler 10 is evacuated, for example, first to very high vacuum using a turbomolecular pump such as pump 14 not open to the mass spectrometers. The entire system can then pump down in its analytical configuration, for example, for a period of time, for example, three hours before the analytical session is begun. When the system is in analytical configuration, released inclusion volatiles from autosampler 10 can be pumped directly through mass spectrometers 12 (See FIG. 5A). That is, gas evolved during analyses can be pumped through the ionization chambers of the mass spectrometers in order to be pumped away. If desired, automated valving can be added so that pump 14 assists in pumpdown between impacting of rock samples.

For operation, the system is maintained at a vacuum of about $10^{-8}$ to about $10^{-6}$ torr. Even during release of volatiles, the pressure will not increase much above $10^{-6}$ torr. Generally, the pumps evacuating the system during analytical configuration maintain low pressures to insure substantially all of released volatiles are passed through mass spectrometers for analysis.

The operation of controller 16 is described in detail below in reference to FIG. 4B.

B2—Determining Composition of Released Volatiles

As indicated, a step of an aspect of the invention relates to determining composition of released fluid inclusion volatiles. Any suitable means for determining composition such as gas chromatography (GC), mass spectroscopy (MS), combined GC/MS and the like can be used. A preferred method of determining composition is illustrated in FIGS. 4A, 4B, 5, 6A and 6B.

Figure 4A:
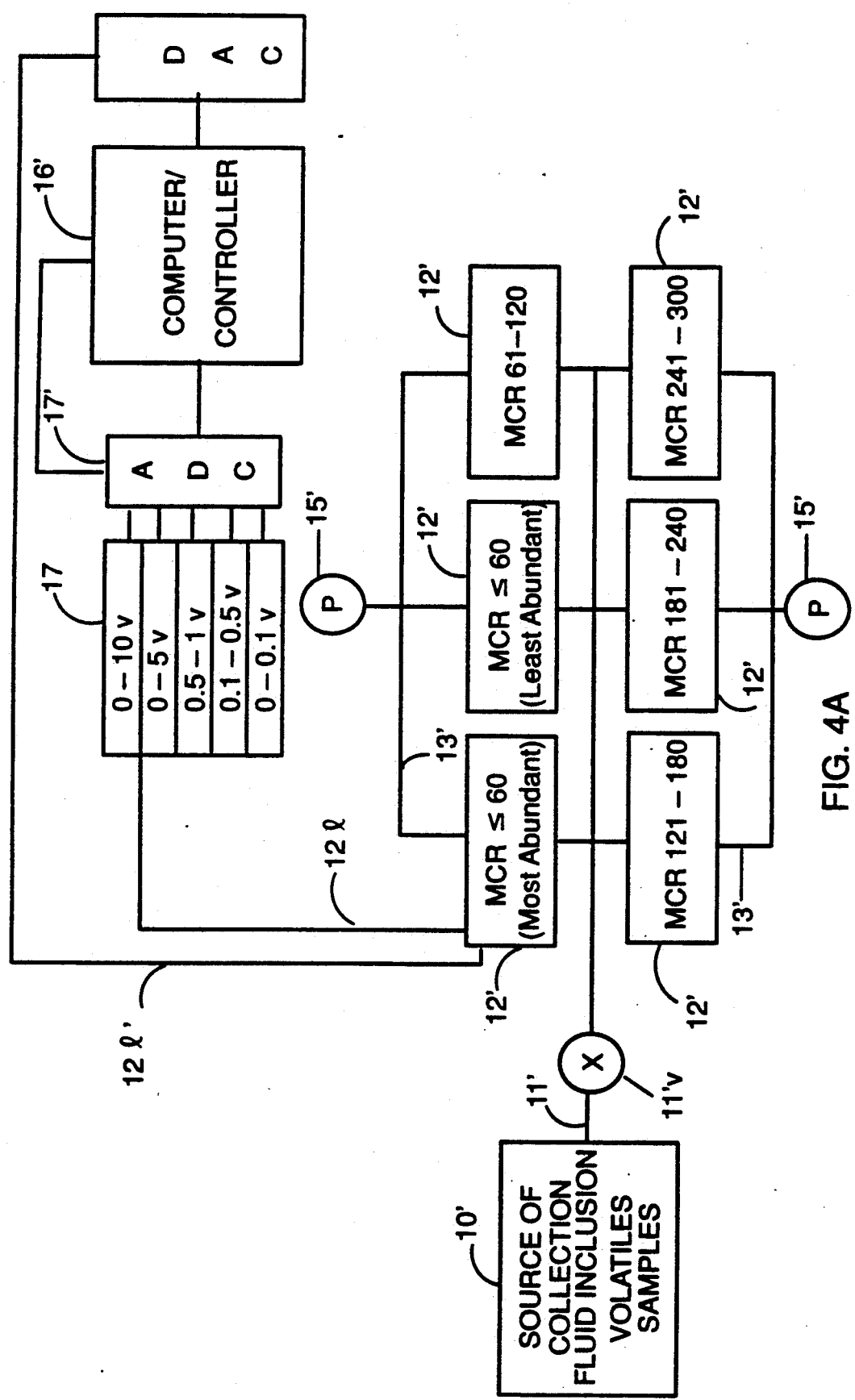
FIG. 4A illustrates schematically a system for mass spectroscopic analysis of collective fluid inclusion volatiles samples.

Referring now to FIG. 4A, FIG. 4A illustrates a preferred system for mass spectrometric analysis of collective fluid inclusion samples. Referring now to FIG. 4A in detail, there is illustrated a source 10' of collective fluid inclusion volatiles samples, such as autosampler 10 in FIG. 3, connected via line 11' having valve 11'v to a preferred arrangement of mass spectrometers 12'. During analytical configuration, valve 11'v is open and samples are being withdrawn as they are released by crushing. Thus, the system depicted in 4A is dynamic, i.e., open to the sampler 10' during sample release. As illustrated, the mass spectrometers are arranged in two banks of three, each bank having a pump 15' for drawing sample from line 11' through each of mass spectrometers 12' via outlet line 13'. Each mass spectrometer is configured to sample a specific set of MCR (mass to charge ratio) responses using the optimum gain for each, for example, as follows:

| Mass Spectrometer | Mass to Charge Ratio Responses Sampled |
|---|---|
| 1 | 2, 16, 17, 18, 28, 44 |
| 2 | 3, 4, 12, 13, 14, 15, 19-27, 29-43, 45-60 |
| 3 | 61-120 |
| 4 | 121-180 |
| 5 | 181-240 |
| 6 | 241-300 |

Generally there are no peaks at MCR 5 to 11. By assigning specific MS to sample a set of MCR responses which have comparable amplitudes, time lost in switching amplifiers for the MS can be minimized. Thus, MS1 samples the most abundant MCR<61 and MS2 samples the least abundant MCR<61.

The 0-10 v signal outline of each mass spectrometer 12' is operably connected to a bank of five signal conditioners 17, each configured for a different optimum gain, discussed in detail below.

The outputs of signal conditioners 17 are provided to analog to digital converter (ADC) 17' and then to computer controller 16'. For simplicity, only the output of one MS 12' is illustrated but the other MS 12' are also so configured.

Since the MS system of FIG. 3A is open to sampler 10' during sampling, volatiles are being passed through the MS system over a period of time dependent on the relative molecular weight of the volatiles and the period of time when volatiles are being released from a particular sample. Accordingly, the MS system is configured and controlled for scanning a range of MCR of interest a multiplicity of times during the period of release of volatiles from each rock sample, and the results from all the multiplicity of scans are summed on an MCR by MCR basis for each rock sample.

As described herein, the MCR range of interest is from about 2-300 MCR to encompass an advantageous range for analysis. Greater or lesser ranges can also be used. Preferably, substantially all or at least a preponderance of ranges such as 2-60, 2-120, 2-180, 2-240, 2-300 and the like are scanned a multiplicity of times as a volatiles sample is released from each rock sample. As described herein, the multiplicity of scans is 256. More or fewer scans can be used, for example, 128. Reduction in number of scans leads to loss of precision and accuracy, but can increase speed of operation.

Figure 4B:
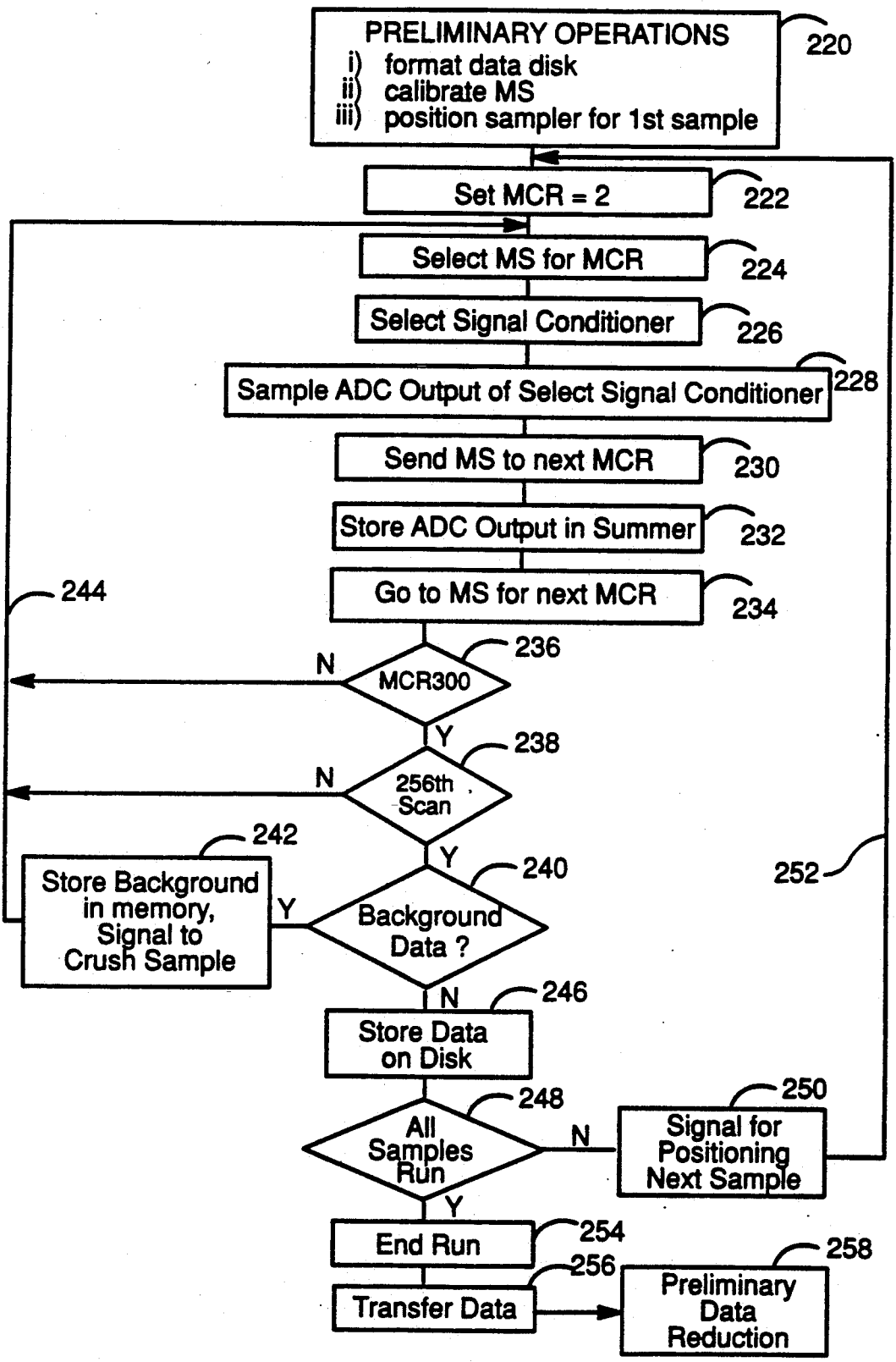
FIG. 4B illustrates, by a simplified flow diagram, control of the autosampler/analysis system of FIG. 4A.

Referring now to FIG. 4B, FIG. 4B illustrates control of the MS system of FIG. 3A integrated with control of the autosampler 10 of FIG. 3. Generally, the system scans sampler 10 or 10' a multiplicity of times during a time when no sample is being released and sums the results on an MCR by MCR basis to provide a background reading. The system then scans sampler 10' a multiplicity of times during a time when a collective volatile sample is being released from a particular rock sample and sums the results on an MCR by MCR basis to provide a sample reading. The system repeats the preceding two steps until a plurality of samples has been run. In a preliminary data reduction step, background readings taken before each sample is read can be removed from the sample readings. The preliminary data reduction is described in more detail below in reference to FIGS. 6A and 6B.

Referring now to FIG. 4B in detail, FIG. 4B illustrates a system for control of sampler 10 and the MS system of FIG. 3A.

Controller 16 can be, for example, a personal computer programmed for controlling autosampler 10, mass spectrometers 12 and for storing composition data produced from mass spectrometer 12 on disk together with apparatus for driving the rams, motor, controlling mass spectrometers and the like. Such equipment can readily be assembled by those skilled in the art for use as described herein. Any suitable controller can be used.

For each rock sample, controller 16 generates signals causing measurements and recording of background data, causing a rock sample to be impacted, causing measurement and recording of background plus fluid inclusion volatiles, causing storing of preliminary recorded data on disk and querying whether all samples have been run. If all samples have not been run, controller 12 generates a signal controlling motor 24 for causing carousel 26 to position for crushing of the next rock sample. When all samples have been run, controller 12 can perform end of run procedures such as releasing the vacuum on the system, data transfer, and the like. The operation of controller 16 is illustrated in more detail in FIG. 4B discussed below.

As indicated at 220 in FIG. 4B, certain preliminary operations can be controlled by controller 16. Thus, controller 16 can generate signals for formatting a data disk in controller 16, for calibrating mass spectrometer system 12, and for positioning carousel 26 for impacting of a predetermined first rock sample.

Step 222 is for setting the beginning of the MCR range (MCR=2). Step 224 is for controller 16 sampling the output of the MS configured for MCR2 and step 226 is for the computer selecting a signal conditioner for optimum gain for MCR 2 signal and causing the selected conditioner output to appear on the output line of ADC 17' where the computer samples it (step 228). Step 230 is for sending the MS to the next MCR to be tested. Step 232 is for storing the sampled ADC in the appropriate summer. The computer then by Steps 234 and 236 are for the computer sampling in the same way via loop 244, the MS assigned to the next MCR until the full range of MCR 2-300 has been scanned.

The step for sending the appropriate MS to the next MCR is illustrated in FIG. 4A by line 121 and in FIG. 4B by step 230. It can be accomplished using controller 16 including a DAC (digital to analog converter). Thus, a personal computer can provide a signal selecting the next MS for the next MCR to a DAC for a particular mass spectrometer. The DAC can then cause the appropriate mass spectrometer to be configured for the next MCR to be read.

By step 238, the full range of MCR of interest is scanned a multiplicity of times for each rock sample, the data for each MCR being summed on an MCR by MCR basis for the multiplicity of scans. After 256 scans, the computer tests whether there was a scan of background data or of sample data by step 240. This can be as simple as determining the set of 256 scans is the second set since impacting the previous rock sample. Upon determining that the readings were of background data, step 242 stores the background data for the sampler in the computer's memory and generates a signal to autosampler 10 causing the first sample to be impacted and returns to step 224.

Steps 224 through 240 are then repeated and when step 240 now responds indicating that sample data have been measured, step 246 stores the sample data on disk. Step 248 inquires whether all samples have been run and if not, by step 250 and loop 252 provides a signal via line 24c (see FIG. 3) to sampler 10 to position the next rock sample for analysis. After step 248 indicates that all samples have been run, step 254 ends the run, and the data can then be transferred if desired (see step 256) to another computer for preliminary data reduction. All of the steps described above can be readily implemented by those skilled in the art of computerized control from the description herein using commercially available equipment.

Figure 5:
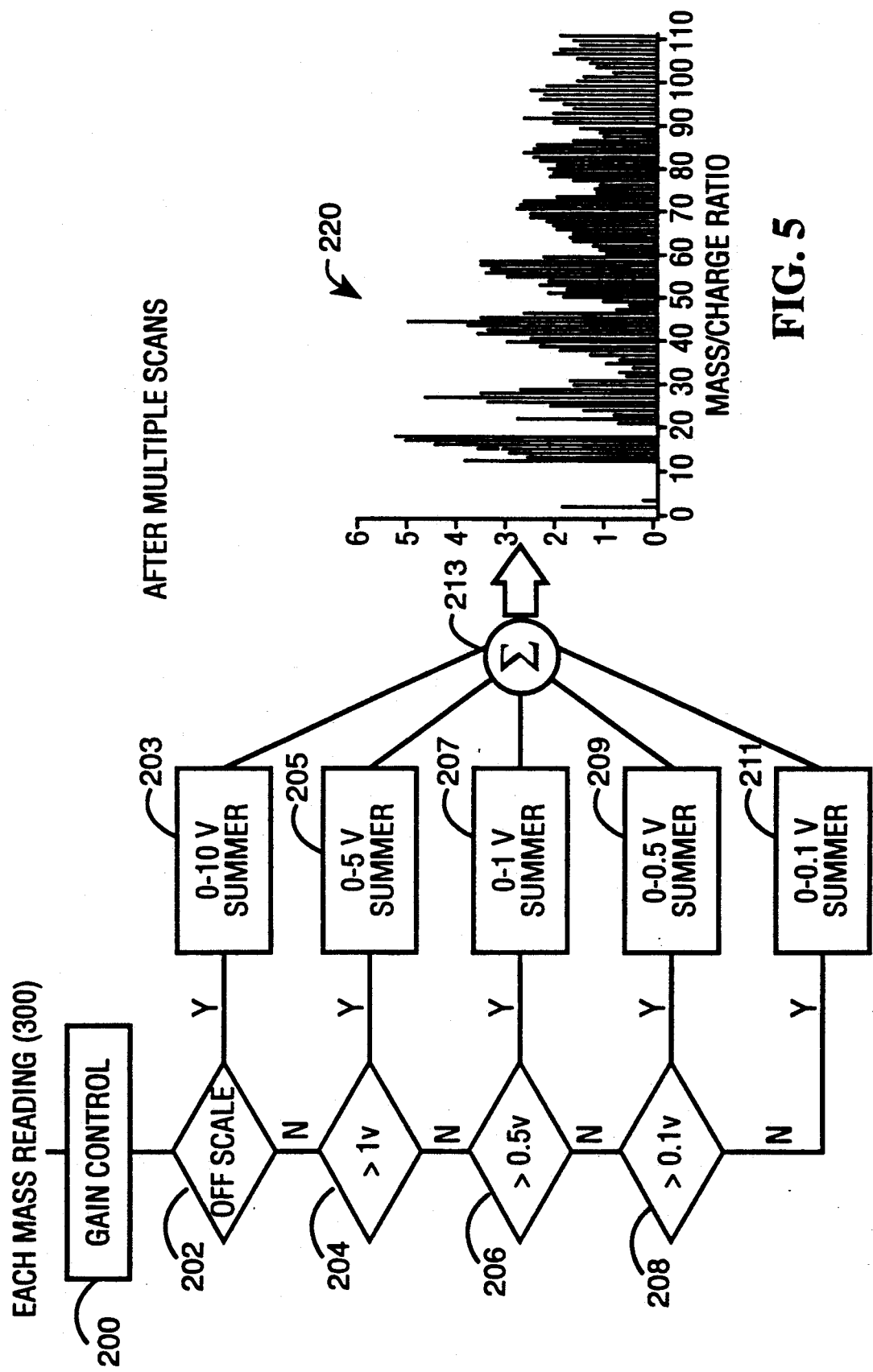
FIG. 5 illustrates, by simplified flow diagram, a system for summing mass to charge ratio (MCR) responses for each of a plurality of scans of a range of MCR for a single collective volatiles sample to produce summed MCR values for the totality of scans for the single collective volatiles sample which can be displayed as an MCR spectrogram.

Referring now to FIG. 5, an autoranging routine is shown for selecting an optimum signal conditioner for each MCR reading and for summing the readings on an MCR by MCR basis. A 0–10 volt signal from each mass spectrometer is sent to a bank of five signal conditioners set at different gains. The gains of the 30 signal conditioners are calibrated using a National Bureau of Standard standard. The computer uses an autoranging routine such as shown in FIG. 5 to select the optimum signal conditioner for each MCR scan. For each MCR reading, a particular signal conditioner is selected by, for example, 0–5 v gain control 200. Then each MCR response is directed to the appropriate memory for summing by steps 202, 204, 206, 208. Thus, if step 202 indicates that the signal s for the particular MCR is >5 v, the response is sampled on the 0–10 v channel and summed using the 0–10 v summer 203. If $1<s<5$, step 204 samples and sums the response using the 0–5 v summer 205. If $0.5<s<1$, step 206 samples and sums the response using the 0–1 v summer 207. If $0.1<s<0.5$, step 208 samples and sums the response using the summer 209; if $<0.1$, using the summer 211. After, for example, 256 mass scans are summed for each MCR in the range of 2–300 MCR, computer 16 can sum the responses for each MCR over all scans and can generate for each collective fluid inclusion volatiles sample a mass spectrogram such as the one shown at 220 in FIG. 5B.

Preferably the abundance of different MCR of an MCR spectrogram are presented in logarithmic scale. This is because linear scale representations make difficult recognition of occurrence of trace elements and compounds useful in characterizing classes of inclusions. The use of a logarithmic scale which enhances MCR responses of trace organic and inorganic volatiles relative to the more abundant components of fluid inclusions is therefore preferred. The MCR spectrogram 220 in FIG. 5 represents such a display in logarithmic scale. Linear or other scales can also be used.

Figure 6A:
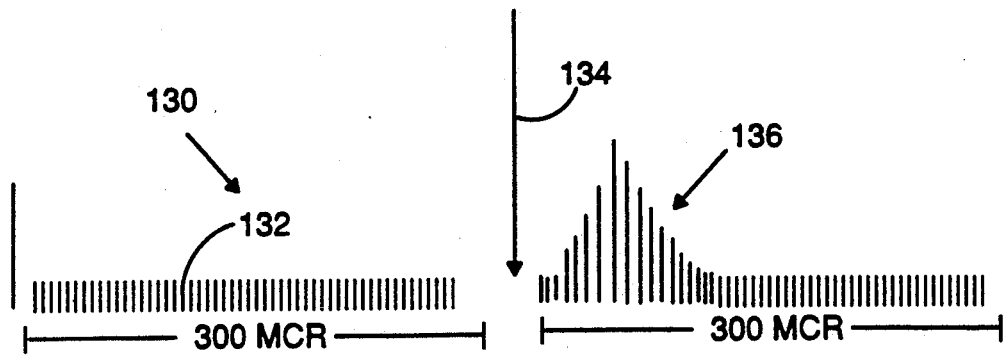
FIG. 6A schematically illustrates measurement of autosampler background data and of autosampler background data plus collective fluid inclusion sample data.
Figure 6B:
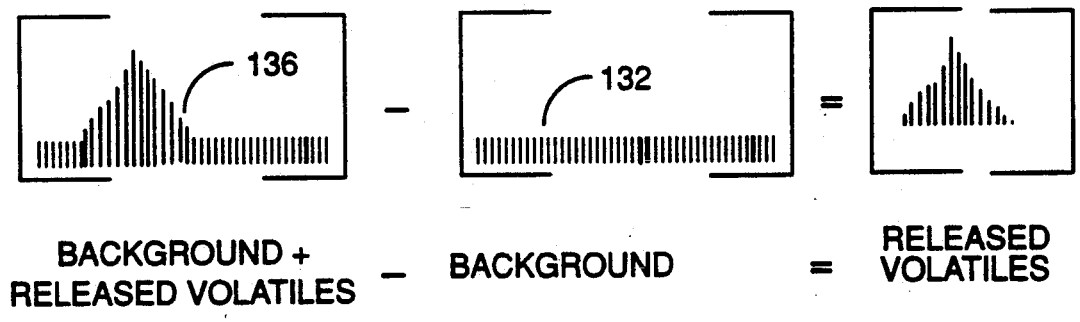
FIG. 6B schematically illustrates distinguishing inclusion from noninclusion gases by subtracting background data from sample data.

Mass spectrograms for autosampler background data and for a sample are also illustrated in a simplified manner at 132 and 136, respectively, in FIGS. 6A and 6B.

During operation, controller 16 reads the output of mass spectrometers 12' 256 times in about 10 seconds as a volatiles sample is being released from an individual rock sample to collect 256 complete MCR spectra from MCR 2 through 300, i.e., for each volatiles sample 256 scans of MCR 2–300 are made. A summer 213, for example, in computer 16, sums the 256 responses from each MCR from all of the multiplicity of scans as they are collected. For each MCR, after selecting the optimum signal conditioner, collecting the data, adding it to the total for that MCR, and storing the result in memory, controller 16 triggers the appropriate mass spectrometer system to proceed to the next MCR. The computer then reads a signal from the mass spectrometers configured to sample that MCR, and so on until 256 MCR scans are summed. A time interval, for example, about 100 microseconds can be allowed between each MCR sampled.

For each rock sample the summed data from the first multiplicity of scans are an analysis of the background gases in the system (see 130 in FIG. 6A).

Once the background is characterized, the computer signals and controls the appropriate air piston one or more times to ram the appropriate steel slug thus impacting the sample (time of occurrence illustrated in FIG. 6A by arrow 134). 256 new scans of 2–300 MCR are initiated each time the rock sample is impacted or while the rock sample is crushed multiple times. The sum of the second and subsequent multiplicity of 256 scans is the analysis of the fluid inclusion gases plus the background, as illustrated by reference numeral 136 in FIG. 6A.

Referring now to FIG. 6B, FIG. 6B illustrates a preliminary data reduction step in which the background gas contribution 132, characterized immediately before impacting each rock sample, is subtracted from data 136 on an MCR by MCR basis for each collective fluid inclusion volatiles sample plus background. This technique is effective for discriminating inclusion from non-inclusion gases so that the final volatiles record is representative of inclusion gases.

In the mass spectrometer, the molecules in each bulk sample are ionized, accelerated, separated according to MCR, and measured. Ionization is usually accompanied by partial fragmentation of the molecules which is characteristic of specific molecules and operating conditions. While fragmentation complicates interpretation—a given molecular weight fragment can be derived from different molecules—it also permits distinguishing between isomers and gives molecular structural information. The output can be various forms of MCR versus abundance records, mass spectrograms, and the like.

The mass values of some fragments encountered in fluid inclusion analysis and source molecules are shown in the following table.

TABLE 1

| MCR Signatures - Inorganic Fluid Inclusion Gases | |
|---|---|
| Inorganic Gases | MCR Signature |
| $H_2$ | 2 |
| He | 4 |
| $H_2O$ | 18 |
| $CO_2$ | 22, 44 |
| Ar | 40 |
| $N_2$ | 28, 14 |
| $NH_3$ | 17 |
| CO | 28 |
| $H_2S$ | 34 |
| $O_2$ | 32 |
| SO(1-3) | 48 |
| COS | 60 |
| $CS_2$ | 76 |
| Ne | 20, 22 |
| HCl | 35, 36, 37, 38 |
| Xe | 129, 130, 131, 132, 134, 136 |

TABLE 2

| Mass Signatures - Organic Fluid Inclusion Gases | |
|---|---|
| Organic Gases | Mass Signature |
| Methane | 15 |
| Ethane | 30 |

TABLE 2-continued

| Mass Signatures - Organic Fluid Inclusion Gases | |
|---|---|
| Organic Gases | Mass Signature |
| Propane | 44 |
| Butane | 58 |
| Benzene | 78 |
| Toluene | 91 |
| Xylene | 105 |
| Triterpenes | 191 |
| Steranes | 217 |

The mass spectra for the higher mass organic compounds becomes complicated with overlapping means spectra peaks, making it difficult to identify single compounds with certainty. Classes of organic compounds, however, share common fragments:

TABLE 3

| MCR Signatures - Higher Mass Organic Compounds | |
|---|---|
| Organic Gases | MCR Signature |
| paraffins | 57 |
| naphthenes | 55 |
| aromatics | 77 |
| toluene | 91 |
| alkylated naphthenes | 97 |

In addition to these peaks, these hydrocarbon families tend to give responses at every 14 mass numbers due to the CH2 repeat in organic polymers:

TABLE 4

| MCR Signatures - Higher Mass Organic Compounds With Repeating $CH_2$ | |
|---|---|
| Organic Gases | MCR Signatures |
| paraffins | 57, 71, 85, 99, 113, 127, etc. |
| naphthenes | 55, 69, 83, 97, 111, 125, etc. |

Figure 2A:
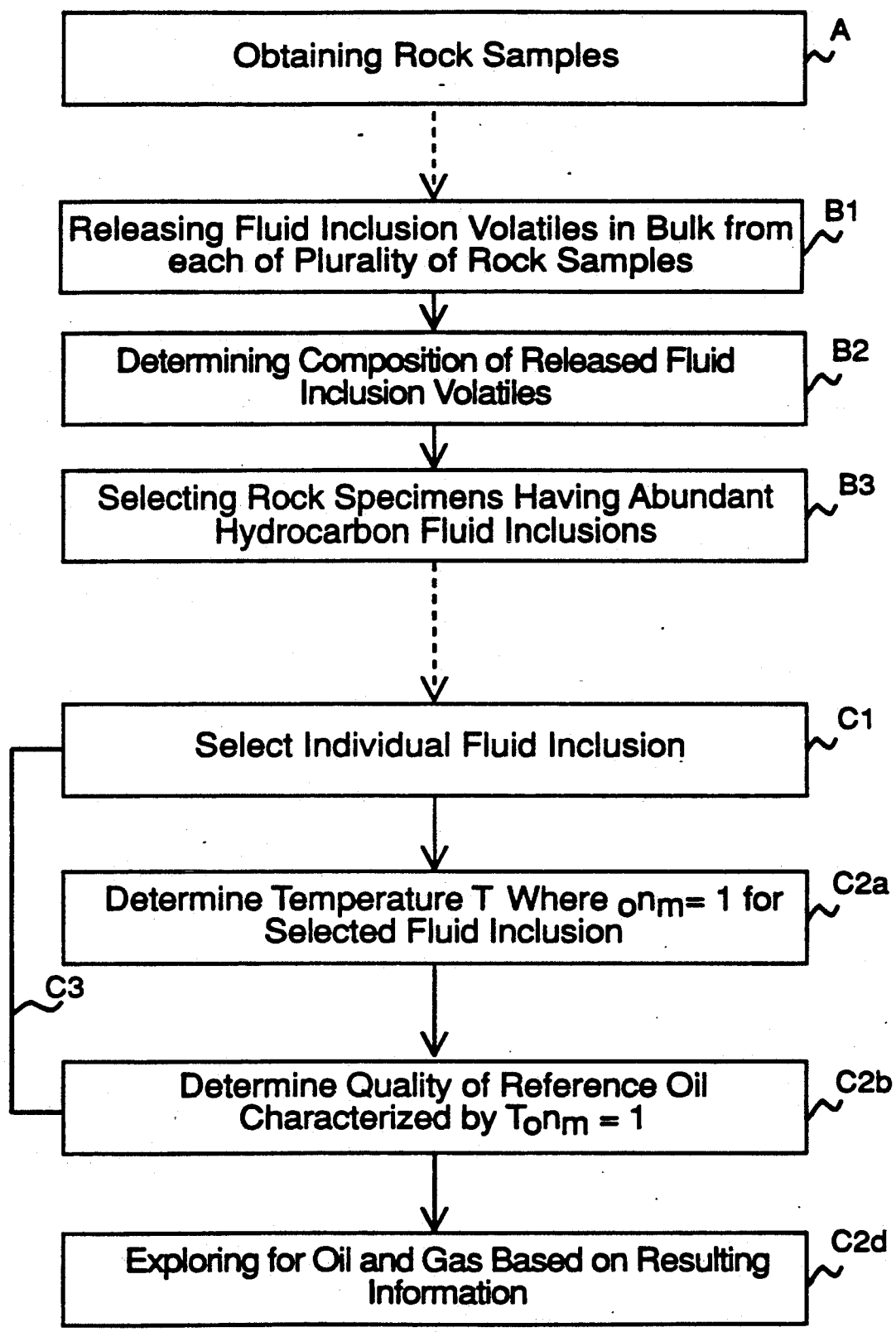
FIG. 2A represents FIG. 1A with steps B and C illustrated in greater detail.

B3—Selecting Rock Specimens Characterized by Selected Fluid Inclusion Composition As indicated in FIGS. 2 and 2A, a step of an aspect of the invention relates to selecting rock specimens characterized by a selected fluid inclusion composition. This can be done in any convenient way such as by inspecting fluid inclusion composition for selected compounds and selecting a rock specimen from a rock sample characterized by the composition. Preferably the selecting step comprises displaying selected composition data as a function of depth or areal location in the earth, identifying one or more depths characterized by greater abundance of an MCR indicator of a class of fluid inclusions, and selecting rock specimens from rock samples corresponding to such depths.

Preferably composition data resulting from analysis of collective fluid inclusion volatiles are displayed as a function of depth along a borehole or of areal location in the earth. Since the composition data are representative of heterogeneous fluid inclusions, MCR can be selected representative of particular compounds of interest and displayed relative to other MCR. Such displays may be referred to as fluid inclusion composition log displays.

In comparing one or more types of molecules to one or more others, such as A to B, one approach is to determine the ratio A/(A+B). This permits a semiquantitative evaluation from well to well. A is referred to herein as normalized with respect to B. Either A or B can represent one or more MCR.

Different displays are useful for different purposes as described in more detail below. Binary displays in which one MCR or group of MCR is compared to another MCR or group of MCR can be used for fluid inclusion log displays. Such binary displays are useful as displaying relative abundance of one or more compounds to one or more others. Referring to FIG. 3A, by measuring and integrating a pressure change during volatiles release, for example, using pressure gauge P, a measure of absolute abundance of the various MCR can also be obtained using the ideal gas law.

Table 5 below illustrates some useful binary displays; however, many other selections for display of relative or absolute abundances of elements and compounds in fluid inclusions can be used in accordance with the invention. Exemplary mapping uses are shown in Table 5; however, all measures can be used as chemical composition markers in appropriate cases. It will be apparent that suitable displays of such data as a function of depth permit rapid selection of rock specimens characterized by particular classes of fluid inclusions which are of technical and economic significance.

TABLE 5

| Binary Mass/Mass Plots | | |
|---|---|---|
| Mass/Mass Ratio | Compound/Compound | Mapping Tool Example |
| 57/57 + 15 | Paraffin/Paraffin + Methane | Oil vs. Gas |
| 57/55 + 57 | Paraffin/Paraffin + Naphthenes | Oil vs. Water Inclusion |
| 91/97 + 91 | Toluene/Alkylated Naphthenes | Composition of Hydrocarbon in Inclusion |
| 34/15 + 34 | $H_2S$/Methane | Productive Faults |
| 34/44 + 34 | $H_2S$/$CO_2$ | Productive Faults |
| 15/18 + 15 | Methane/Water | Hydrocarbon vs Water |
| 57/44 + 57 | Paraffin/$CO_2$ | Migration Zones, Seals |
| 4/4 + 2 | Helium/Hydrogen + Helium | Stratigraphic Marker |
| 28/44 + 28 | Nitrogen/$CO_2$ | Paleo Air Zones |
| 15/59 + 15 | Methane/Methane + $CO_2$ | Migration Zones, Seals |
| 40/40 + 41 | Argon 40/Hydrocarbon fragment | Paleo Air Zones |

While binary ratios, tertiary ratios and the like can be advantageously used to select classes of fluid inclusions, relative abundance of indicators of selected classes of inclusions are preferably selected and displayed relative to the rock samples themselves, i.e., abundance (moles of gas) per weight or volume unit of rock sample ("raw" or "absolute" response). A suitable linear scale is preferred, such as a scale which scales a peak indicative of greatest abundance of a series of rock samples to full scale on the display.

Thus, it is preferred to display MCR indicators of oil relative to rock samples (i.e., raw responses) since it has been found that such responses reliably indicate occurrence of, for example, oil containing inclusions even where normalized A/(A+B) responses do not. When raw responses are to be obtained, it becomes more important to insure that the volume or weight of each rock sample is approximately equal. Good results have been obtained, however, even with somewhat disparate volumes of rock or weight samples.

Thus, by inspecting fluid inclusion compositions or by displaying selected compositions as a function of depth or areal location, rock samples characterized by fluid inclusions of selected compositions can be identified and a rock specimen obtained of the corresponding rock sample. Thus, rock specimens characterized by abundant fluid inclusions representing paleo exposure zones, hydrocarbons and the like can be identified to depth or areal location using appropriate plots such as, for example, illustrated in Table 5. Then, a sample of corresponding rock at the selected location can be selected for further analysis in accordance with the invention.

According to an aspect of the invention, see step B' of FIG. 1A and step B3 of FIG. 2A, rock specimens can be selected using composition data representative of oil fluid inclusions.

Figure 7:
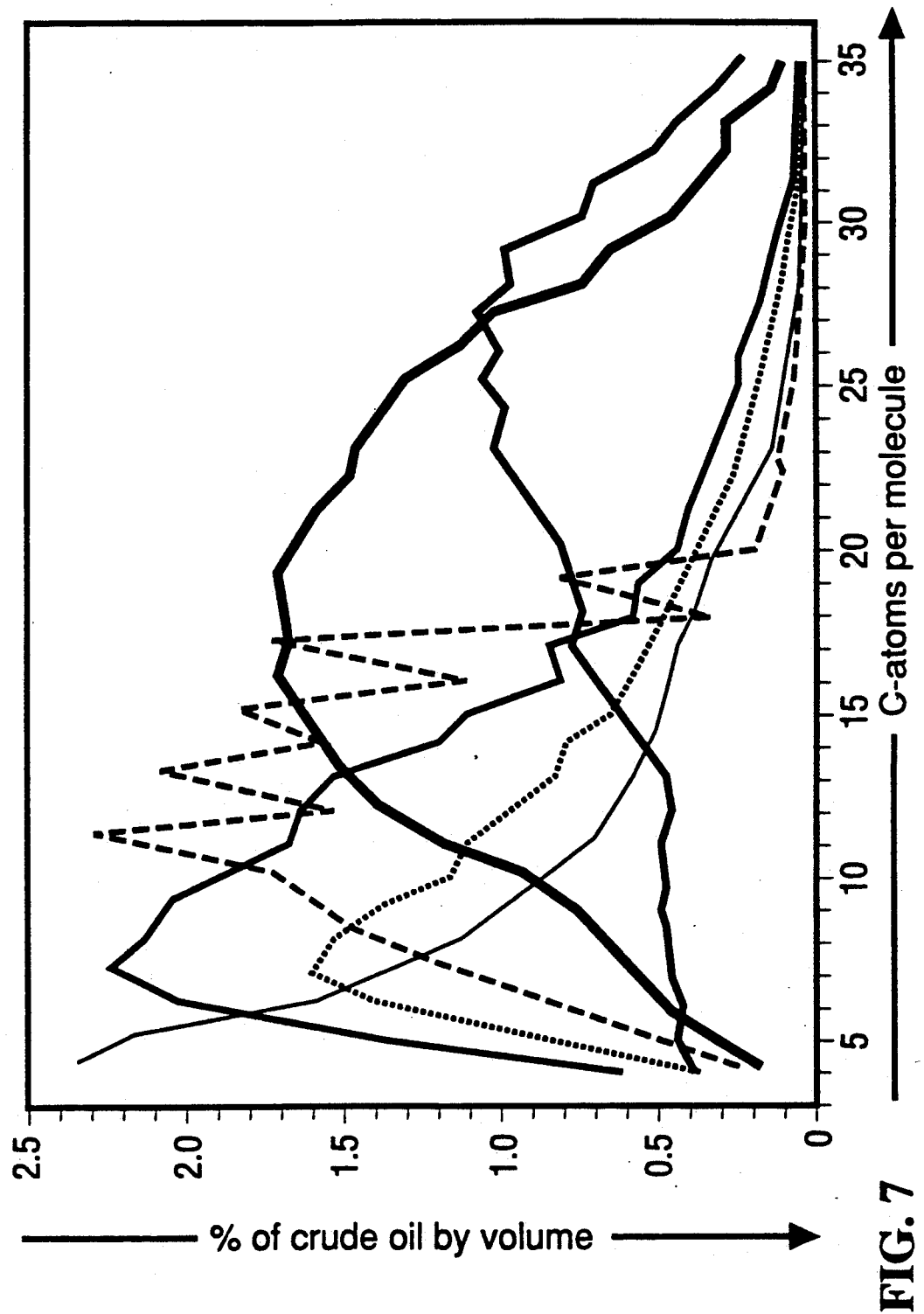
FIG. 7 illustrates carbon chain distributions of a number of different crude oils.

Referring now to FIG. 7, FIG. 7 illustrates carbon chain distribution for a series of different crude oils. In plotting composition information as a function of depth or areal location preliminary to selecting rock specimens characterized by abundant oil inclusions, any MCR representative of occurrence of oil can be selected. Broadly as can be seen in FIG. 7, an MCR fragment representative of $C_5$ to $C_{35}$ can be selected, preferably $C_8$ to $C_{20}$, most preferably in the range of $C_{10}$ to $C_{17}$ (for example, $C_{12}$) since carbon chain lengths in this range are significantly represented in all of the illustrated crudes.

Referring now to FIG. 8A, FIG. 8A illustrates results of analysis of a plurality of mineral samples for a well.

Figure 8B:
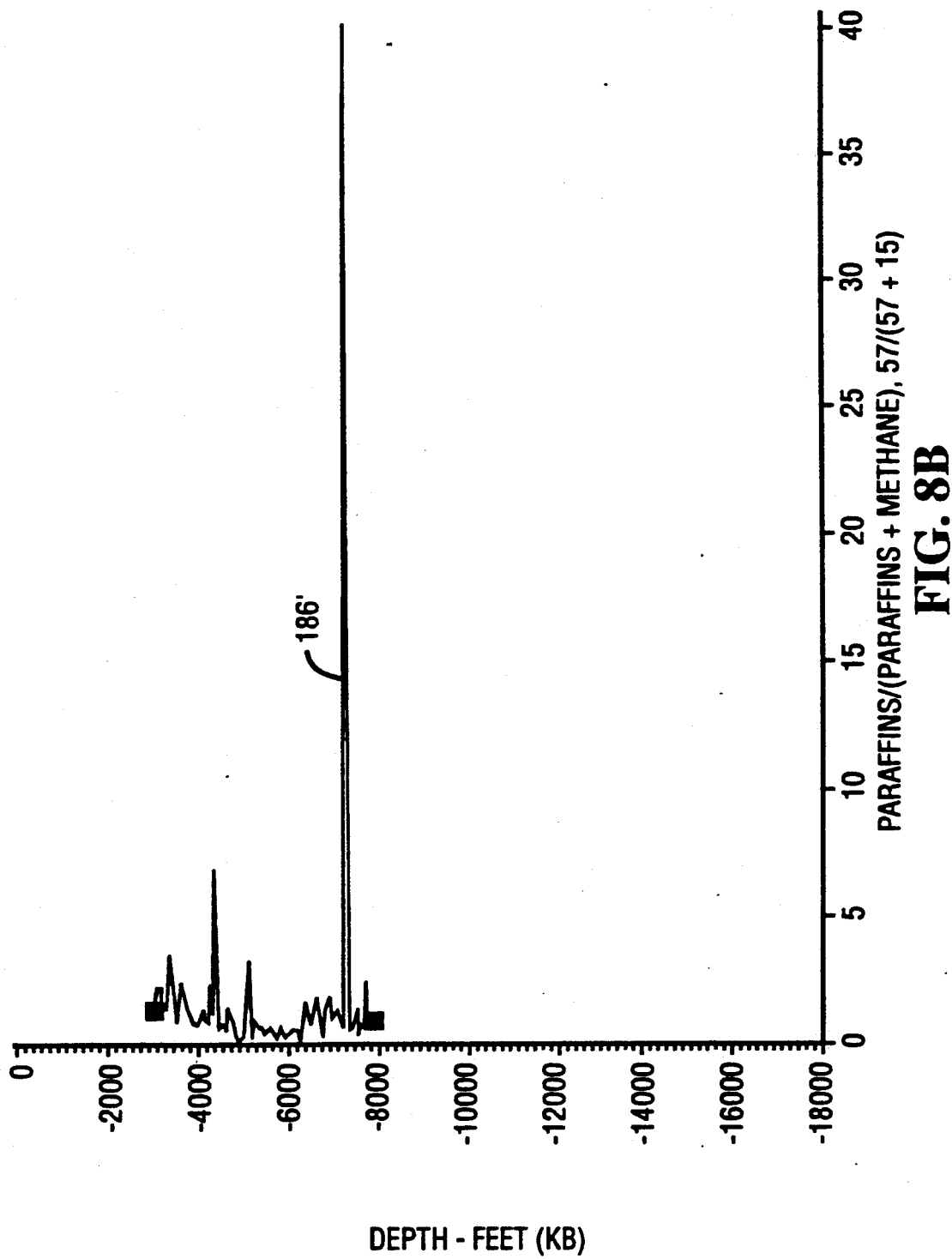
FIG. 8B illustrates for the well of FIG. 8B a plot of depth versus paraffin normalized to methane as an indicator of occurrence of oil in collective fluid inclusion volatiles.

FIG. 8A indicates at reference numerals 180, 182, 184, 186 at depths shown occurrence of MCR 170 used as an indicator of oil. MCR 170 corresponds to $C_{12}H_{26}$. FIG. 8B displays the ratio of paraffins to paraffins plus methane also shows an occurrence at 186' to corresponding to 186 in FIG. 8A. However, the FIG. 8B display fails unambiguously to indicate occurrences at shallower depths corresponding to reference numerals 180, 182, 184 of FIG. 8A. This illustrates that displays of raw abundance of MCR indicators may be preferable to displays of normalized indicators.

Figure 9A:
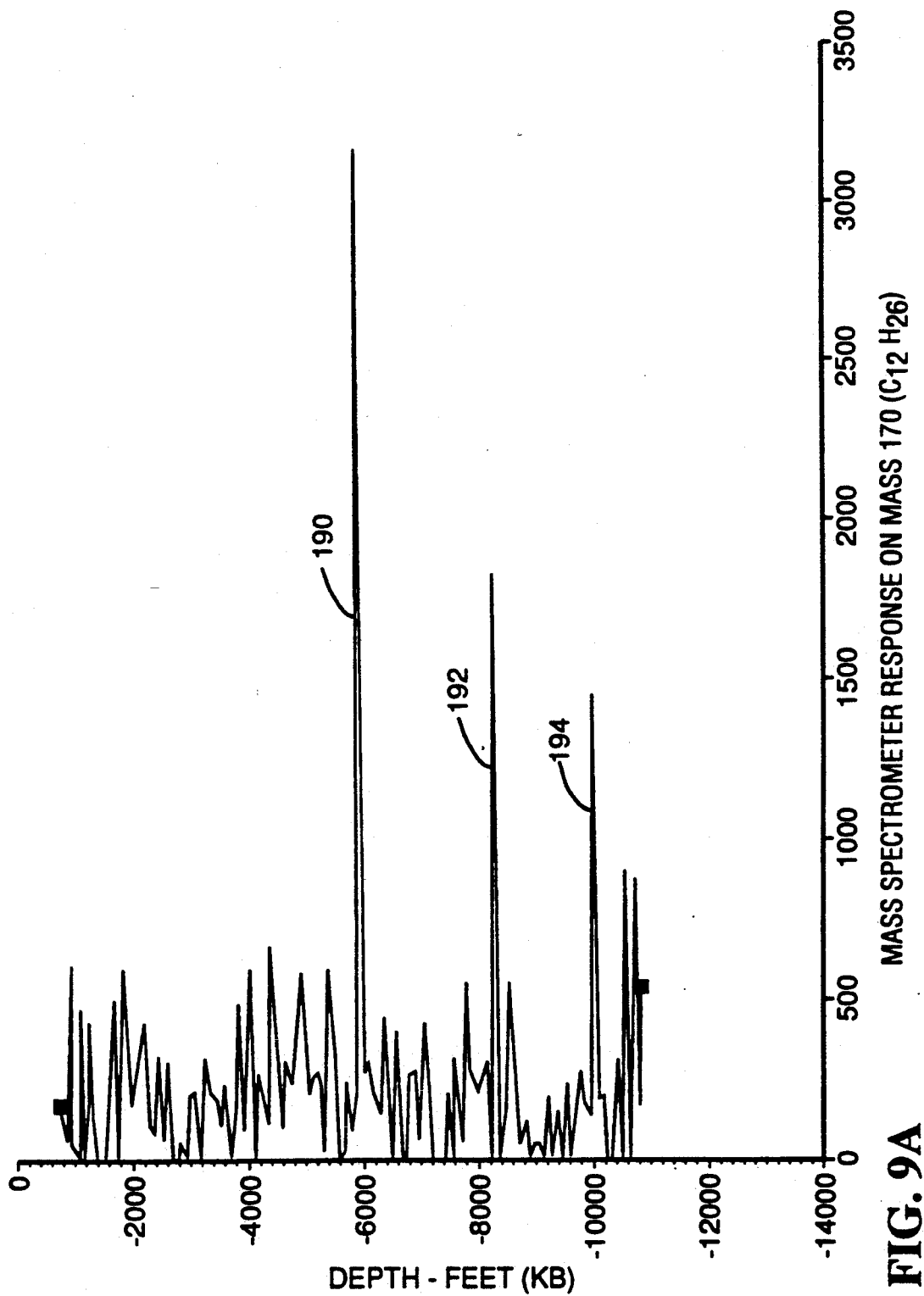
FIG. 9A illustrates for a second well a plot of depth versus an MCR indicator of oil in collective fluid inclusion volatiles samples.
Figure 9B:
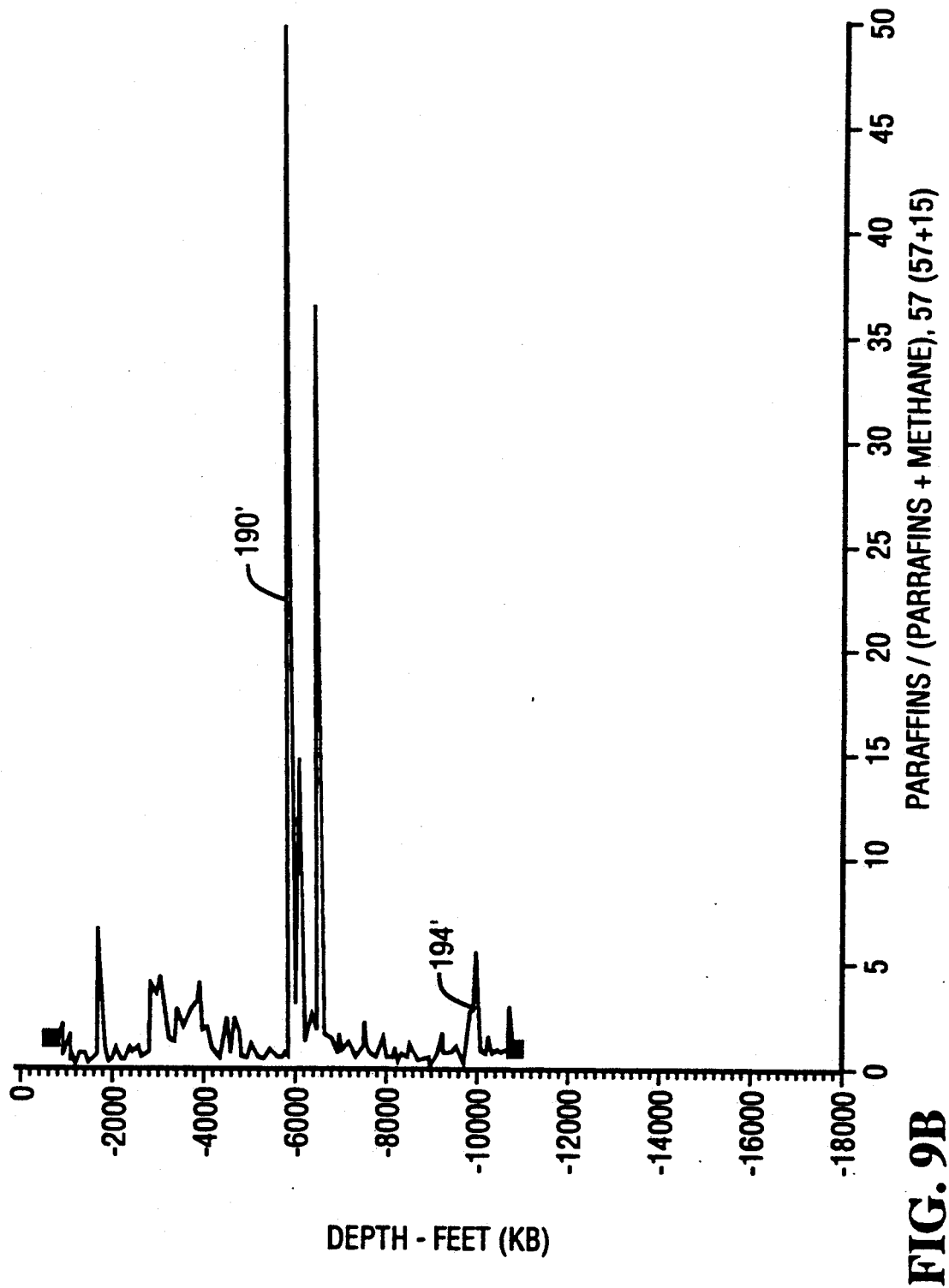
FIG. 9B illustrates for the well of FIG. 9A a plot of depth versus paraffin normalized relative to methane as an indicator of oil in collective fluid inclusion volatiles samples.
Figure 9C:
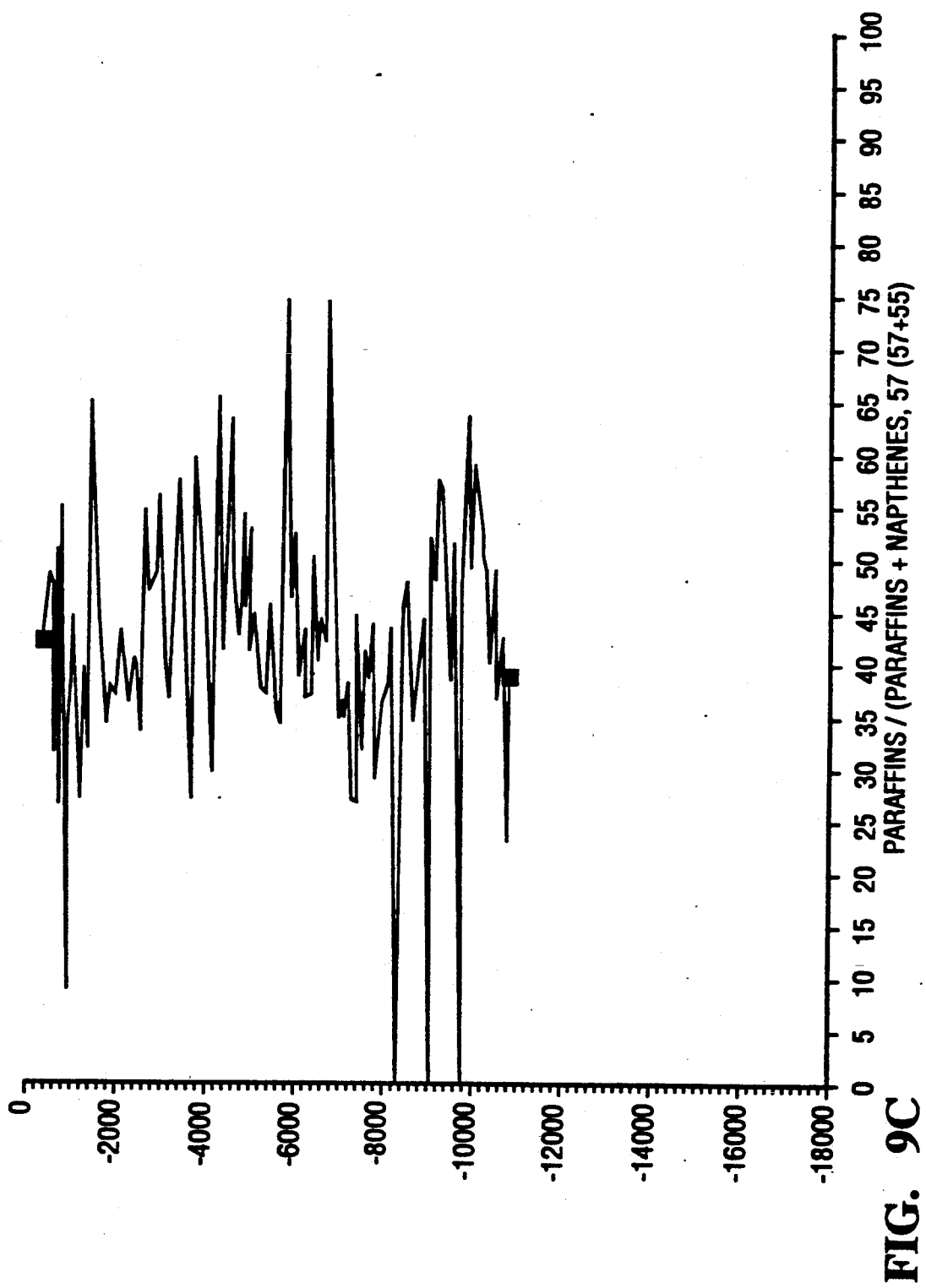
FIG. 9C illustrates for the well of FIG. 9C a plot of depth versus paraffins normalized relative to naphthenes.

Referring now to FIGS. 9A, 9B, 9C, these figures illustrate various measures of fluid inclusion compositions for a second well. FIG. 9A illustrates occurrence of MCR 170 as a function of depth indicating increase of occurrence at reference numerals 190, 192, 194. FIG. 9B illustrates variations in the ratio of paraffins to paraffins plus methane and has an indicator of increased abundance at reference numeral 190' corresponding to reference numeral 190 of FIG. 9A. Reference numeral 194' on FIG. 9B likewise though less striking corresponds to peak 194 on FIG. 9A. Reference numeral 192 of 9A has no corresponding peak on FIG. 9B. Referring now to FIG. 9C, a display of paraffins plus paraffins plus naphthenes fails unambiguously to indicate any of the indicators of increased relative abundance of FIG. 9A. This again illustrates that displays of raw abundance of selected MCR indicators can be preferable to normalized displays.

C1—Selecting Individual Fluid Inclusions or Specific Classes of Fluid Inclusions A step of an aspect of the invention relates to selecting individual fluid inclusions or specific classes of fluid inclusions (See steps C, C', C1 of FIGS. 1, 1A, 2, and 2A respectively).

A rock specimen selected as described herein based on occurrence of compositions characteristic of selected class of inclusions can be used to prepare a thin polished mineral section as is known to those skilled in the art. However, any specimen in which individual fluid inclusions can be identified and selected and subjected to further analysis according to the invention can be used. Thus, the individual or class of fluid inclusions can be selected using a microscope from among the various classes described herein. For example, primary or secondary inclusions or oil-, gas-, aqueous or mixed fluid inclusions, inclusions formed at different times or in different minerals can be selected for further characterization. The step of selecting individual or classes of fluid inclusions is readily accomplished using standard petrographic techniques and need not be further described here.

C2—Further Characterizing Composition of Selected Individual or Classes of Inclusions A step of an aspect of the invention (see FIGS. 1, 1A at step C and FIGS. 2, 2A at steps C2, C2a, C2b) relates to further characterizing composition of selected individual or classes of fluid inclusions in the selected rock specimen.

The further characterization can be by rupturing and analyzing the composition of individual selected fluid inclusions as described in U.S. Pat. Nos. 4,856,351 and 4,898,831 (both incorporated herein by reference), by freezing the fluid inclusion, removing covering mineral by ion abrasion, and analyzing composition by electron microprobe as described in U.S. Pat. No. 4,916,314 (incorporated herein by reference) and other methods such as those known to those skilled in the art.

According to a preferred aspect of the invention, selected oil inclusions are further characterized with regard to quality (API or specific gravity) of oil contained therein.

Thus, the invention in one aspect relates to a method for determining quality of oil in selected individual oil fluid inclusions (see steps C2a, C2b of FIG. 2A).

As used herein, oil or hydrocarbon quality is used to refer to any characteristic of hydrocarbon which can be reliably related to variations in refractive index of oil as a function of temperature, for example, specific gravity, API gravity and the like. The specific gravity of oil is normally specified not as a fraction in relation to water taken at "1" but as API gravity. API gravity is specific gravity measured in degrees on an American Petroleum Institute scale. On the API scale, oil with the least specific gravity has the highest API gravity. Other things being equal, the higher the API gravity, the greater the economic value of oil. Most crude oils range from 27 degrees to 35 degrees API gravity.

The API gravity of oil is a function of its refractive index at constant temperature. Light travels through denser oils, i.e., those having low API gravities, slower than it does through less dense high API gravity oils. Therefore, high API gravity oils have low refractive indices, and vice versa, at constant temperature. Therefore, if one could measure the refractive index of an oil in a fluid inclusion at a known temperature, one would know the API gravity of the oil. However, making a direct measurement of refractive index of oil in a fluid inclusion is impractical.

Nevertheless, the refractive index of oil is a strong function of temperature inasmuch as the density of the oil is strongly temperature dependent. Also, the refractive indexes of minerals are relatively temperature insensitive, i.e., mineral densities and refractivities are not strongly dependent on temperature. Further, at a given constant temperature API gravity an oil and its refractive index are strongly correlative. Therefore, the temperature at which the index of refraction of oil and an adjacent host mineral are equal is a strong function of API gravity.

Referring to FIG. 2A, the step of determining quality of individual oil fluid inclusions includes a step C1 in which an individual fluid inclusion is selected; a step C2a in which the temperature $T_{onm=1}$ is determined for which the refraction index of hydrocarbon in the fluid inclusion is about equal to the refractive index of the adjacent mineral; and a step C2b in which the quality of a reference oil having $T_{onm=1}$ for a comparable mineral is used as a measure of hydrocarbon quality in the selected individual fluid inclusion. Stated alternatively, this step is one of determining the quality (API gravity) of an oil whose refractive index at $T_{onm=1}$ is about equal to the refractive index of the oil or of the adjacent mineral. Optionally, by step C3 these steps C1, C2a, C2b can be repeated for other selected individual fluid inclusions.

C2a—Determining $T_{onm=1}$ for a Selected Fluid Inclusion

The temperature at which the refractive index of the oil equals that of its host mineral can be easily measured by skilled person using a microscope equipped with a microscope heating/freezing stage. Such microscopes and stages are commercially available.

According to this aspect of the invention, an individual fluid inclusion can be selected by examination under magnification using for example a microscope. Preferably, a portion of a rock specimen selected as discussed above is used to prepare a thin polished mineral section. The preparation of such thin sections are well known in petrographic arts. However, any selected rock specimen in which a hydrocarbon fluid inclusion can be effectively observed during heating and cooling can be used, for example, mineral grains, cleavage sections and the like.

The rock specimen can be placed on a heating-cooling stage of a microscope, and a hydrocarbon inclusion of a type and generation of interest selected. The inclusion can be observed during heating and cooling until the temperature at which the refractive index of the oil and of the surrounding mineral is about equal. This temperature is the temperature at which the Becke line ceases to move or changes direction. The Becke line is a bright line, visible under a microscope, that separates substances of different refractive indexes. The bright Becke line appears to move toward the material (mineral or inclusion) of higher refractivity as the tube of the microscope is raised and toward the less refractive material when the tube is lowered. At $T_{onm}$, the Becke line does not move as focal plane changes as the microscope tube is racked up and down. Alternatively, $T_{onm}$ can be determined by observing the temperature at which the Becke line changes direction from toward to away (or vice versa) from a selected material in a given focal plane. The Becke test is a standard petrographic test for refractivity measurements and can readily be used for determining $T_{onm}$ in accordance with the invention.

Those skilled in the art will recognize that this temperature corresponds to the temperature at which the Becke lines caused by difference in refractive index as between hydrocarbon in fluid inclusion and adjacent mineral change direction of bending. Alternatively, the temperature corresponds to the temperature at which the inclusion which previously appeared in negative or positive relief relative to adjacent mineral disappears, at another temperature again to become visible in positive or negative relief, respectively.

Becke lines are well known to those skilled in the art and need no further discussion here. See, for example, Bloss, *An Introduction to the Methods of Optical Crystallography* (1961) pages 50–52 which is incorporated herein by reference.

Figure 10A:
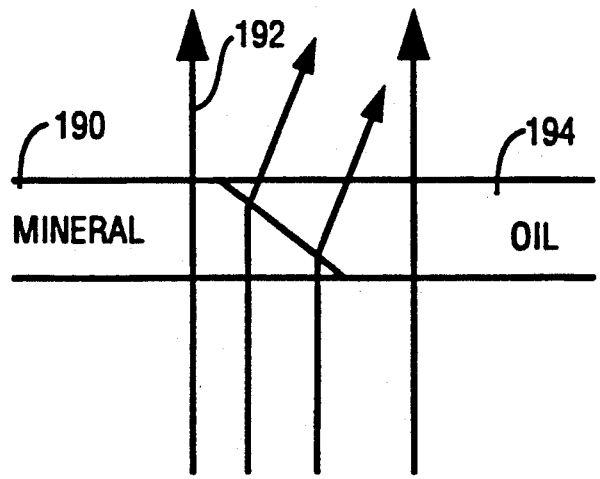
FIGS. 10A, 10B and 10C illustrate light bending due to refraction at the oil-mineral interface of a fluid inclusion at temperatures where the oil has a greater refractive index than the adjacent mineral (FIG. 10A), a lesser refractive index than the adjacent mineral (FIG. 10C) and approximately the same refractive index (FIG. 10B).
Figure 10B:
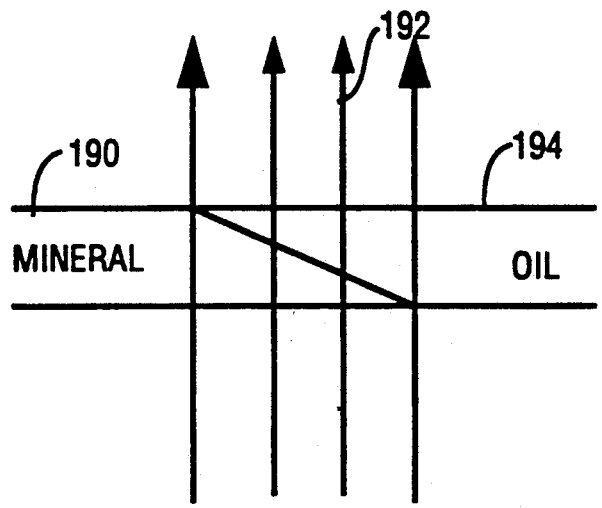
Figure 10C:
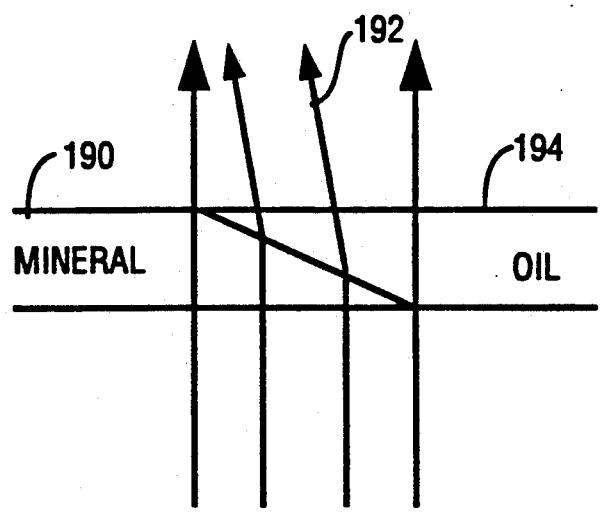

FIG. 10A illustrates the bending of light rays 192 at a temperature where mineral 190 adjacent hydrocarbon fluid inclusion 194 has a smaller index of refraction than the hydrocarbon. FIG. 10B illustrates a temperature where the refractive indexes are about equal, i.e., $T_{onm=1}$. FIG. 10C illustrates a temperature where adjacent mineral 190 has a greater index of refraction than hydrocarbon inclusion 194.

C2b—Determining Quality of Reference Oil for $T_{onm=1}$

According to this aspect of the invention, a series of hydrocarbon oils of known quality (API gravity) at a temperature $t = T_{onm=1}$ are evaluated to determine which oil has a refractive index about equal to mineral adjacent a selected hydrocarbon fluid inclusion of interest.

Figure 11A:
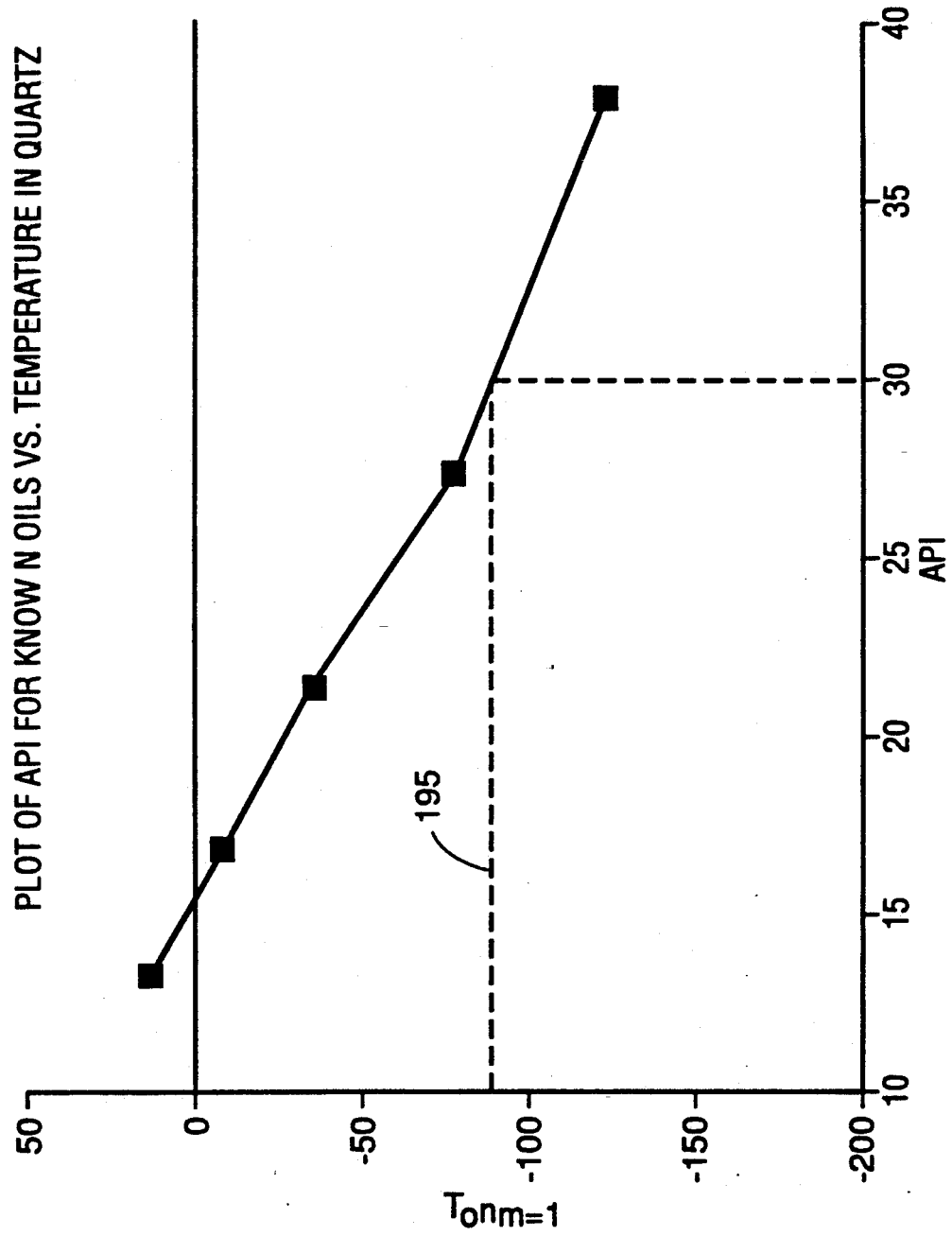
FIG. 11A illustrates the relationship between API gravity and the temperatures for which the refractive indexes of a series of reference oils are about equal to that of a non birefringent mineral such as quartz.

For each mineral, for example, quartz, feldspar, dolomite, calcite, and the like, a series of oils can be tested and $T_{onm=1}$ determined for each and plotted as a function of quality, for example, specific gravity, API gravity, and the like, as illustrated in FIG. 11A. Thus, FIG. 11A illustrates the relationship between the following oils and the temperature at which the refractive index of the oil is equal to the refractive index of ground quartz.

| Oil | t °C. | API Gravity |
|---|---|---|
| 1 | 12 | 13.2 |
| 2 | −10 | 17.1 |
| 3 | −37 | 21.5 |
| 4 | −80 | 27.6 |
| 5 | −125 | 37.6 |

To illustrate, dashed line 195 in FIG. 11A indicates that a fluid inclusion having $T_{onm=1}$ at about 90° C. has an API gravity of 30.

Figure 11B:
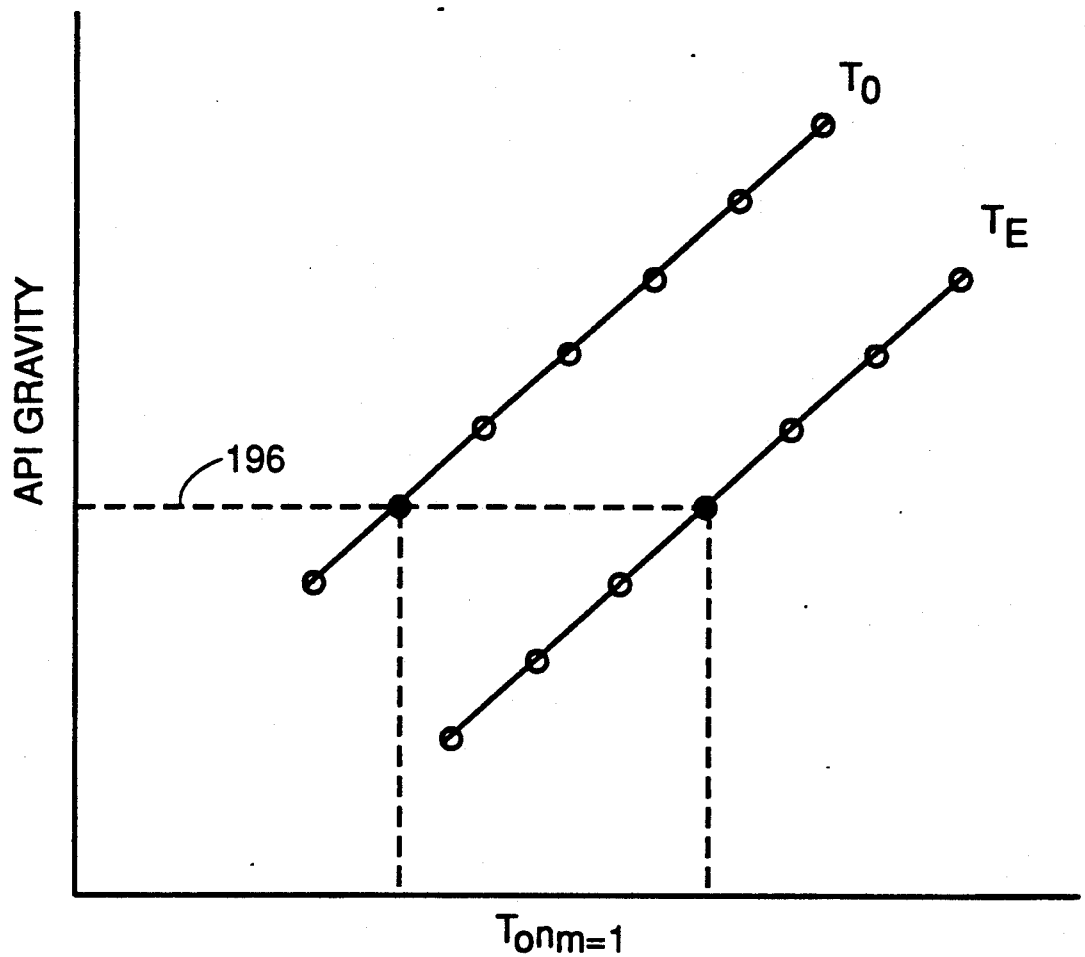
FIG. 11B illustrates the relationship shown in FIG. 11A for a birefringent mineral.

Quartz, unlike calcite, dolomite, tourmaline, and the like, is characterized by low birefringence. For more highly birefringent minerals, the curve of FIG. 11A may be doubled as illustrated in FIG. 11B in which $T_o$ represents the curve for the ordinary ray and $T_e$ represents the curve for the extraordinary ray.

As indicated by dashed line 196, either curve $T_o$ or $T_e$ may be used in determining $T_{onm=1}$ however, it is important to know which of $T_o$ or $T_e$ is being used. By using a polarizing microscope and by adjusting the polarizers on the microscope to pass only one of $T_o$ or $T_e$ as is known in the art of optical crystallography, confusion can be avoided. Alternatively, the desired temperature T can be measured for each of $T_o$ and $T_e$.

A series of oils versus temperatures at which refractive index of oil and mineral are about the same will be preferably run for each mineral of interest. For example, in dealing with a relatively homogeneous mineral sample, a portion of the sample can be ground, and T for a reference series of oils determined. For nonhomogeneous samples, it may be necessary, for example, to dissolve away certain minerals and run the series of sample oils for remaining mineral, to excise certain minerals by micromanipulation, and the like.

A series of oils vs. temperature of equal refractivity for oil and mineral for one set of mineral samples may serve for other sets where the minerals are comparable, that is, have about the same refractive indexes. For example, where quartz is the adjacent mineral and it is known that substitutions in quartz have little effect on refractive index, curves as illustrated in FIG. 11 for one set of mineral samples can be used for numerous other sets. For minerals having refractive indexes which vary significantly with substituents, for example, calcite, dolomite, and the like, it may be preferable to run a series for each set of samples. By using the invention, a library of curves may be developed and accumulated so that in most cases, after identifying mineral adjacent a selected inclusion an appropriate quality temperature relation curve can be selected and used.

D. Using Resulting Information in Oil and Gas Exploration

As indicated, a step D of the aspect of the invention illustrated in FIGS. 1, 1A, 2 and 2A is using the resulting compositional information in exploring for oil and gas.

Where oil quality is determined in accordance with a specific aspect of the invention, this step can include, for example, comparing the thus determined quality of oil in inclusions with oil known to occur in the region. If the two or more oils have similar quality, this is an indication that the migrating oil may have contributed to the accumulation known to occur in the region. Conversely, if the two or more oils have disparate quality measurements, this may indicate that other accumulations of oil not yet found may occur in the region.

Similarly, fluid inclusion evidence of paleo environments can be used in the exploration for oil and gas just as other geological evidence of those environments are used. Since use of paleo environment indicators generally in exploring for oil and gas is well known to those skilled in the art, further detailed description is not needed.

EXAMPLE I

An offshore area has two dry wells for which drill cuttings are available. It is desired to determine whether oil has migrated through the subsurface for determining whether to pursue exploration and development in an adjacent area.

Drill cuttings from two offshore dry wells are evaluated to identify formations having hydrocarbon fluid inclusions.

The procedure of sections B1, B2, and B3 above is used to select formation characterized by occurrence of hydrocarbon fluid inclusions.

Referring now to FIGS. 8A and 8B, these figures represent occurrence of oil indicator ($C_{12}$ MCR fragment) relative to the rock sample (FIG. 8A) and of paraffin normalized relative to methane (FIG. 8B). Use of the procedure narrows the search for rock samples having abundant hydrocarbon inclusions to rock samples obtained at depths corresponding to reference numerals 180, 182, 184, 186.

The FIG. 8B plot confirms that zone 186 (about 7400 ft) may have oil inclusions, but fails to differentiate the shallow zone 180 above 3800 ft which is seen in FIG. 8A. This illustrates an advantage of the FIG. 8A plot.

Rock specimens are taken at 3760 ft (zone 180) and at 7360 ft (zone 186). Thin sections are prepared and observed under fluorescence microspectrophotometry (FM). Both samples contain numerous fluorescent oil filled fluid inclusions.

By microthermometry, the minimum temperatures at which the inclusions might have formed are determined to be 302° F. at 7360 ft and 194° F. at 3760 ft.

The API gravity is determined in accordance with the invention to be 38 API at 7360° F. and 28 API at 3760° F.

The Example illustrates that the invented technique can be used to find and characterize quality of oil inclusions.

EXAMPLE II

A second dry well is illustrated by FIGS. 9A, 9B, and 9C. No oil shows are observed in this well. FIG. 9A illustrates raw occurrence (relative to rock) of oil indicator $C_{12}$ MCR 170 fragment at depths corresponding to zones 190, 192, 194. FIG. 9B illustrates abundance of paraffins normalized relative to methane and confirms zones 190 and 194 by zones 190' and 194' respectively. FIG. 9C illustrates occurrence of paraffins normalized relative to naphthenes. Although some correspondence of peaks may be noted, it is apparent that the peaks in FIG. 9A are relatively more visible in FIG. 9A. This Example also indicates that the occurrence of paraffin normalized to methane is effective for identifying some but not all zones. This illustrates the advantage of plots of the form of FIG. 9A.

Rock specimens corresponding to zone 192 at depth 8940 ft are obtained, polished thin sections prepared and observed by fluorescence microspectrophotometry (FM). Numerous oil inclusions are observed in healed fractures in the quartz grains. The API gravity of three inclusions is determined using the invented technique and is found to range from 28 to 32 API. This is the first indicator of oil, possibly migration, in an area previously only known characterized by biogenic gas. This illustrates the advantage of the method of the invention in determining whether migration has occurred in an area and through which strata.

The invention has been described in detail and illustrated with specific embodiments but is not limited thereto, but by the claims appended hereto interpreted in accordance with applicable principles of law.

What is claimed is:

1. A method comprising:
    determining quality of hydrocarbons in selected individual hydrocarbon fluid inclusions which can provide quality estimates without extraction by steps including:
    selecting an individual fluid inclusion in a rock specimen containing hydrocarbon fluid inclusions;
    determining temperature $T_{onm=1}$, being the temperature at which the refractive index of hydrocarbon in the fluid inclusion is about equal to the refractive index of mineral adjacent the fluid inclusion;
    determining quality of a reference oil having $T_{onm=1}$ for mineral having same or substantially the same index of refraction; and
    using the thus determined quality of a reference oil as a measure of the quality of the hydrocarbon in the selected fluid inclusion.

2. The method of claim 1 comprising:

measuring temperatures $T_{onm=1}$ for each of a series of reference oils having known quality relative to a mineral;

measuring the temperature $T_{onm=1}$ for a selected hydrocarbon fluid inclusion; and determining the quality of the selected hydrocarbon fluid inclusion from measurement of $T_{onm=1}$ for the series of reference oils and for the selected hydrocarbon fluid inclusion.

3. The method of claim 1 comprising:

determining the quality of the selected hydrocarbon fluid inclusion from measurement of $T_{onm=1}$ for the series of reference oils and for the selected hydrocarbon fluid inclusion.

4. The method of claim 1 wherein $T_{onm=1}$ of a hydrocarbon fluid inclusion in a rock specimen is determined using the Becke line method.

5. The method of claim 1 wherein the mineral is birefingent and a selected one or both of the ordinary ray and extraordinary ray is used for determining $T_{onm=1}$ for each of the hydrocarbon fluid inclusion and the series of reference oils.

6. The method of claim 1 further comprising:

comparing thus determined quality of hydrocarbon fluid inclusion with quality of oil known to occur in region from which rock sample containing hydrocarbon fluid inclusion was obtained.

7. The method of claim 6 wherein the comparison indicates that the hydrocarbon fluid inclusion oil quality is about the same as oil known to occur in said region; and comprising further exploring for accumulations of said oil of known quality.

8. The method of claim 6 wherein the comparison indicates that the hydrocarbon fluid inclusion oil quality is different from that of oil known to occur in said region; and comprising further exploring for accumulations of said oil of different quality.

* * * * *

UNITED STATES PATENT AND TRADEMARK OFFICE
CERTIFICATE OF CORRECTION

PATENT NO. : 5,241,859
DATED : Sep. 7, 1993
INVENTOR(S) : Michael P. Smith

It is certified that error appears in the above-indentified patent and that said Letters Patent is hereby corrected as shown below:

| Col. | Line | |
|---|---|---|
| 13 | 13 | "overlapping means spectra peaks," should read --overlapping mass spectra peaks,-- |

Signed and Sealed this

Fifth Day of July, 1994

Attest:

BRUCE LEHMAN

Attesting Officer

Commissioner of Patents and Trademarks